US012779048B2

(12) United States Patent
Nevala et al.

(10) Patent No.: US 12,779,048 B2
(45) Date of Patent: Nov. 3, 2026

(54) ANTIBODY-NANOPARTICLE COMPLEXES AND METHODS FOR MAKING AND USING THE SAME

(71) Applicant: Mayo Foundation for Medical Education and Research, Rochester, MN (US)

(72) Inventors: Wendy K. Nevala, Oronoco, MN (US); Svetomir N. Markovic, Rochester, MN (US); Liyi Geng, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 559 days.

(21) Appl. No.: 18/043,722

(22) PCT Filed: Sep. 1, 2021

(86) PCT No.: PCT/US2021/048737
§ 371 (c)(1),
(2) Date: Mar. 1, 2023

(87) PCT Pub. No.: WO2022/051414
PCT Pub. Date: Mar. 10, 2022

(65) Prior Publication Data

US 2023/0338574 A1 Oct. 26, 2023

Related U.S. Application Data

(60) Provisional application No. 63/073,627, filed on Sep. 2, 2020.

(51) Int. Cl.

| | |
|---|---|
| ***A61K 47/69*** | (2017.01) |
| ***A61K 9/19*** | (2006.01) |
| ***A61K 31/337*** | (2006.01) |
| ***A61K 31/4745*** | (2006.01) |
| ***A61K 31/704*** | (2006.01) |
| ***A61K 47/64*** | (2017.01) |
| ***A61K 47/68*** | (2017.01) |
| ***B82Y 5/00*** | (2011.01) |
| ***B82Y 30/00*** | (2011.01) |

(52) U.S. Cl.
CPC ............ *A61K 47/6929* (2017.08); *A61K 9/19* (2013.01); *A61K 31/337* (2013.01); *A61K 31/4745* (2013.01); *A61K 31/704* (2013.01); *A61K 47/643* (2017.08); *A61K 47/6849* (2017.08); *B82Y 5/00* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 5,270,163 | A | 12/1993 | Gold et al. |
| 5,475,096 | A | 12/1995 | Gold et al. |
| 5,582,981 | A | 12/1996 | Toole et al. |
| 5,840,867 | A | 11/1998 | Toole et al. |
| 6,011,020 | A | 1/2000 | Gold et al. |
| 6,051,698 | A | 4/2000 | Janjic et al. |
| 6,147,204 | A | 11/2000 | Gold et al. |
| 6,180,348 | B1 | 1/2001 | Li |
| 6,699,843 | B2 | 3/2004 | Pietras et al. |
| 9,427,477 | B2 | 8/2016 | Markovic et al. |
| 9,446,148 | B2 | 9/2016 | Markovic et al. |
| 9,757,453 | B2 | 9/2017 | Markovic et al. |

FOREIGN PATENT DOCUMENTS

| | | | | |
|---|---|---|---|---|
| JP | 2016-531094 | A | 10/2016 | |
| JP | 2018-516895 | A | 6/2018 | |
| WO | WO 2012/154861 | A2 | 11/2012 | |
| WO | WO 2014/055415 | A1 | 4/2014 | |
| WO | WO 2015/191969 | A1 | 12/2015 | |
| WO | WO 2015/195476 | A1 | 12/2015 | |
| WO | WO 2016/057554 | A1 | 4/2016 | |
| WO | WO 2017/031368 | A1 | 2/2017 | |
| WO | WO 2017/176265 | A1 | 10/2017 | |
| WO | WO 2018/048816 | A1 | 3/2018 | |
| WO | WO-2018048958 | A1 * | 3/2018 | ......... A61K 47/6851 |

OTHER PUBLICATIONS

Allen, "Ligand-targeted therapeutics in anticancer therapy," Nature Reviews Cancer, Oct. 2002, 2(10):750-763.
Alley et al., "Contribution of Linker Stability to the Activities of Anticancer Immunoconjugates," Bioconjugate Chemistry, Mar. 2008, 19(3):759-765.
Arakawa et al., "Protein-Solvent Interactions in Pharmaceutical Formulations," Pharmaceutical Research, Mar. 1991, 8(3):285-291.
Bird et al., "Single-Chain Antigen-Binding Proteins," Science, Oct. 1988, 242(4877):423-426.
Butterfield et al., "Identification of a peptide-peptide binding motif in the coating of nab-paclitaxel nanoparticles with clinical antibodies: bevacizumab, rituximab, and trastuzumab," Scientific Reports, Nov. 2017, 7:14476, 9 pages.
Chang et al., "Preparation, characterization and evaluation of in vitro release of folate-conjugated carboplatin and paclitaxel-loaded bovine serum albumin tumor-targeting nanoparticles," Bulletin of Botanical Research, 2013, 33(4):484-489.

(Continued)

*Primary Examiner* — Brian Gangle
(74) *Attorney, Agent, or Firm* — Fish & Richardson P.C.

(57) ABSTRACT

Provided herein are nanoparticles complexed with binding agents and/or therapeutic agents (e.g., antibody-complexed albumin-bound paclitaxel/doxorubicin nanoparticles and antibody-complexed albumin-bound paclitaxel/SN38 nanoparticles) and pharmaceutical compositions thereof. Additionally, provided herein are methods of making nanoparticles complexed with binding agents and/or therapeutic agents (e.g., antibody-complexed albumin-bound paclitaxel/doxorubicin nanoparticles and antibody-complexed albumin-bound paclitaxel/SN38 nanoparticles) and methods of treating cancer in a patient in need thereof.

8 Claims, 20 Drawing Sheets

Specification includes a Sequence Listing.

(56) References Cited

OTHER PUBLICATIONS

Cleland et al., "The development of stable protein formulations: a close look at protein aggregation, deamidation, and oxidation," Critical Reviews in Therapeutic Drug Carrier Systems, Jan. 1993, 10(4):307-377.
Deguchi et al., "Effect of Methotrexate-Monoclonal Anti-Prostatic Acid Phosphatase Antibody Conjugate on Human Prostate Tumor," Cancer Research, Aug. 1986, 46(8):3751-3755.
Hobbs et al., "Regulation of transport pathways in tumor vessels: Role of tumor type and microenvironment," Proceedings of the National Academy of Sciences of the United States of America, Apr. 1998, 95(8):4607-4612.
Hunkapiller et al., "The growing immunoglobulin gene superfamily," Nature, Sep. 1986, 323(6083):15-16.
Huston et al., "Protein engineering of antibody binding sites: recovery of specific activity in an anti-digoxin single-chain Fv analogue produced in *Escherichia coli*," Proceedings of the National Academy of Sciences, Aug. 1988, 85(16):5879-5883.
International Search Report and Written Opinion in International Appln. No. PCT/US2021/048737, mailed on Jan. 5, 2022, 10 pages.
Jain et al., "Delivering nanomedicine to solid tumors," Nature Reviews Clinical Oncology, Sep. 2010, 7(11):653-664.
Julien et al., "Utilization of monoclonal antibody-targeted nanomaterials in the treatment of cancer," MAbs, Sep. 2011, 3(5):467-478.
Lanzavecchia et al., "The use of hybrid hybridomas to target human cytotoxic T lymphocytes," European Journal of Immunology, Jan. 1987, 17(1):105-111.
Nevala et al., "Antibody-Targeted Chemotherapy for the Treatment of Melanoma," CancerResearch, Apr. 2016, 76(13):3954-3964.
Office Action in JP Appln. No. 2023-514416, mailed on Sep. 1, 2025, 13 pages, with English Translation.
Schrama et al., "Antibody targeted drugs as cancer therapeutics," Nature Reviews Drug Discovery, Jan. 2006, 5(2):147-159.
Thao et al., "Doxorubicin and paclitaxel co-bound lactosylated albumin nanoparticles having targetability to hepatocellular carcinoma," Colloids and Surfaces B: Biointerfaces, Jan. 2017, 152:183-191.
Yuan et al., "Vascular Permeability in a Human Tumor Xenograft: Molecular Size Dependence and Cutoff Size," Cancer Research, Sep. 1995, 55(17):3752-3756.

* cited by examiner

Dox:Taxol® 1:1

50ug:50ug

1:3

25ug:75ug

1:9

10ug:90ug

Paclitaxel (Taxol®)

20-Acetoxy-4-deacetyl-5-epi-20, O-secotaxol
(The Meerwein Product of Paclitaxel)

Non-toxic form of paclitaxel (NTP)

| Group 1 | Group 2 | p-value |
|---|---|---|
| Saline | NIC 15 | 0.003** |
| aPDL1 | NIC 15 | 0.005** |
| Irinotecan | NIC 15 | 0.0003** |
| NTP | NIC 15 | 0.006** |
| SN38 7.5 | NIC 15 | 0.0007** |
| SN38 15 | NIC 15 | 0.0028** |
| Nab 7.5 | NIC 15 | 0.03* |
| Nab 15 | NIC 15 | 0.49 |
| PDL1+Nab 15 | NIC 15 | 0.30 |
| NIC 7.5 | NIC 15 | 0.06 |
| SN38 15 | Nab 15 | 0.013* |
| SN38 7.5 | Nab 7.5 | 0.07 |
| SN38 7.5 | NIC 7.5 | 0.0002*** |
| Nab 7.5 | NIC 7.5 | 0.13 |

| Treatment | Median Survival |
|---|---|
| Saline | 28 |
| a-PDL1 | 34 |
| Irinotecan 15 | 30 |
| NTP | 24.5 |
| SN38 7.5 | 30 |
| SN38 15 | 42.5 |
| Nab 7.5 | Undefined |
| Nab 15 | Undefined |
| PDL1+Nab 15 | Undefined |
| NIC 7.5 | Undefined |
| NIC 15 | Undefined |

| | Saline | a-PDL1 | Irinotecan | NTP | SN38 7.5 | SN38 15 | Nab 7.5 | Nab 15 | PDL1+Nab 15 | NIC 7.5 | NIC 15 |
|---|---|---|---|---|---|---|---|---|---|---|---|
| # alive | 2 | 2 | 4 | 4 | 6 | 8 | 9 | 5 | 8 | 8 | 10 |
| # deaths/events | 3 | 8 | 6 | 6 | 4 | 2 | 1 | 1 | 2 | 2 | 0 |

SEQUENCE LISTING

```
<160> NUMBER OF SEQ ID NOS: 2

<210> SEQ ID NO 1
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 1

Gln Met Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Tyr Ser Trp Val Arg Gln Ala Pro Gly Gln Gly Leu Glu Trp Met
        35                  40                  45

Gly Gly Ile Ile Pro Ser Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

-continued

```
His Glu Ala Leu His Asn His Tyr Thr Gln Lys Ser Leu Ser Leu Ser
        435                 440                 445

Pro Gly Lys
    450


<210> SEQ ID NO 2
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 2

Ser Tyr Val Leu Thr Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Leu Val Trp Asp Ser Ser Ser Asp His
                85                  90                  95

Arg Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

ANTIBODY-NANOPARTICLE COMPLEXES AND METHODS FOR MAKING AND USING THE SAME

CROSS-REFERENCE TO RELATED APPLICATIONS

This patent application is a U.S. National Stage Filing under 35 U.S.C. § 371 of International Patent Application Serial No. PCT/US2021/048737 filed Sep. 1, 2021, which claims the benefit of the priority date of U.S. Provisional Application No. 63/073,627 filed Sep. 2, 2020; priority to each of which is claimed, and each of which is incorporated by reference herein in its entirety.

SEQUENCE LISTING

This application contains a Sequence Listing that has been submitted electronically as an ASCII text file named "087735-0341_SL txt." The ASCII text file, created on May 11, 2026, is 6,251 bytes in size. The material in the ASCII text file is hereby incorporated by reference in its entirety.

FIELD OF THE INVENTION

This disclosure relates to novel compositions of binding agents and carrier proteins and methods of making and using the same, in particular, as a cancer therapeutic.

BACKGROUND

Chemotherapy remains a mainstay for systemic therapy for many types of cancer. Most chemotherapeutics are only slightly selective to tumor cells, and toxicity to healthy proliferating cells can be high (Allen™. (2002) *Cancer* 2:750-763), often requiring dose reduction and even discontinuation of treatment. In theory, one way to overcome chemotherapy toxicity issues as well as improve drug efficacy is to target the chemotherapy drug to the tumor using antibodies that are specific for proteins selectively expressed (or overexpressed) by tumors cells to attract targeted drugs to the tumor, thereby altering the biodistribution of the chemotherapy and resulting in more drug going to the tumor and less affecting healthy tissue. Despite 30 years of research, however, specific targeting rarely succeeds in the therapeutic context.

Conventional antibody drug conjugates (ADC) are designed with a toxic agent linked to a targeting antibody via a synthetic protease-cleavable linker. The efficacy of such ADC therapy is dependent on the ability of the target cell to bind to the antibody, the linker to be cleaved, and the uptake of the toxic agent into the target cell (Schrama, D. et al. (2006) *Nature reviews. Drug discovery* 5:147-159).

Nanoparticle complexes comprising nab-paclitaxel (ABRAXANE®) non-covalently linked to an anticancer antibody have been shown to be effective against melanoma and other cancers and to be more effective than the components of the complex administered alone or administered simultaneously but separately (U.S. Pat. Nos. 9,427,477; 9,446,148; 9,757,453).

Antibody-targeted chemotherapy promised advantages over conventional therapy because it provides combinations of targeting ability, multiple cytotoxic agents, and improved therapeutic capacity with potentially less toxicity. Despite extensive research, clinically effective antibody-targeted chemotherapy remains elusive: major hurdles include the instability of the linkers between the antibody and chemotherapy drug, reduced tumor toxicity of the chemotherapeutic agent when bound to the antibody and the inability of the conjugate to bind and enter tumor cells. In addition, these therapies did not allow for flexible control over the size of the antibody-drug conjugates.

SUMMARY

The present invention is based in part on the development of nanoparticle complexes comprising an anticancer binding agent non-covalently linked to a carrier protein comprising paclitaxel and a therapeutic agent. The nanoparticle complexes described herein surprisingly have increased stability and increased toxicity to cancer cells in vitro compared to nanoparticle complexes made of an anticancer binding agent non-covalently linked to a carrier protein comprising paclitaxel only. Without being bound by any theory, it is thought that the enhanced stability and toxicity of the nanoparticle complexes described herein may further improve biodistribution to favor drug deposition in the tumor and further increase clinical efficacy. Additionally, nanoparticle complexes comprising an anticancer binding agent non-covalently linked to a carrier protein comprising paclitaxel derivative (which is less toxic than paclitaxel) and a therapeutic agent have increased toxicity in vivo compared to nanoparticle complexes made of an anticancer binding agent non-covalently linked to a carrier protein comprising paclitaxel derivative only or compared to nanoparticle complexes comprising carrier protein, paclitaxel derivative and a therapeutic agent.

In an aspect, provided herein is a nanoparticle complex comprising a carrier protein, a binding agent with binding specificity for an anti-cancer epitope, and a therapeutically effective amount of a therapeutic agent (e.g. doxorubicin or SN38) and paclitaxel, wherein the nanoparticle complex has been pre-formed in vitro by mixing an aqueous carrier protein-therapeutic agent-paclitaxel nanoparticle with the binding agent under conditions to form the nanoparticle complex, such that the nanoparticle complex has anti-cancer binding specificity.

In another aspect, provided herein is a nanoparticle complex comprising a carrier protein, a binding agent with binding specificity for an anti-cancer epitope, and a therapeutically effective amount of a therapeutic agent (e.g. doxorubicin or SN38) and paclitaxel derivative, wherein the paclitaxel derivative is less toxic than paclitaxel, and wherein the nanoparticle complex has been pre-formed in vitro by mixing an aqueous carrier protein-therapeutic agent-paclitaxel nanoparticle with the binding agent under conditions to form the nanoparticle complex, such that the nanoparticle complex has anti-cancer binding specificity.

In yet another aspect, provided herein is a pharmaceutical composition comprising a pharmaceutically acceptable carrier and nanoparticle complexes, said nanoparticle complexes comprising a carrier protein, a binding agent with binding specificity for an anti-cancer epitope, and a therapeutically effective amount of a therapeutic agent (e.g. doxorubicin or SN38) and paclitaxel, wherein the nanoparticle complex has been pre-formed in vitro by mixing an aqueous carrier protein-therapeutic agent-paclitaxel nanoparticle with the binding agent under conditions to form the nanoparticle complex, such that the nanoparticle complex has anti-cancer binding specificity.

In another aspect, provided herein is a pharmaceutical composition comprising a pharmaceutically acceptable carrier and nanoparticle complexes, said nanoparticle complexes comprising a carrier protein, a binding agent with binding specificity for an anti-cancer epitope, and a therapeutically effective amount of a therapeutic agent (e.g. doxorubicin or SN38) and paclitaxel derivative, wherein the paclitaxel derivative is less toxic than paclitaxel, and wherein the nanoparticle complex has been pre-formed in vitro by mixing an aqueous carrier protein-therapeutic agent-paclitaxel nanoparticle with the binding agent under conditions to form the nanoparticle complex, such that the nanoparticle complex has anti-cancer binding specificity.

In another aspect, provided herein is a lyophilized composition comprising nanoparticle complexes, each of the nanoparticle complexes comprising a carrier protein, a binding agent with binding specificity for an anti-cancer epitope, and a therapeutically effective amount of a therapeutic agent and paclitaxel, said nanoparticle complexes being lyophilized, and wherein upon reconstitution with an aqueous solution the nanoparticle complexes are capable of binding to the anti-cancer epitope in vivo.

In yet another aspect, provided herein is a lyophilized composition comprising nanoparticle complexes, each of the nanoparticle complexes comprising a carrier protein, a binding agent with binding specificity for an anti-cancer epitope, and a therapeutically effective amount of a therapeutic agent and paclitaxel derivative, wherein the paclitaxel derivative is less toxic than paclitaxel, said nanoparticle complexes being lyophilized, and wherein upon reconstitution with an aqueous solution the nanoparticle complexes are capable of binding to the anti-cancer epitope in vivo.

In another aspect, provided herein is a method for treating cancer in a subject in need thereof, the method comprising administering to the subject a therapeutically effective amount of the nanoparticle complex or pharmaceutical composition, as described above, thereby treating the cancer.

In another aspect, provided herein is a method for treating cancer in a subject in need thereof, the method comprising reconstituting the lyophilized composition of the nanoparticle complex in a pharmaceutically acceptable excipient to form a reconstituted nanoparticle composition and administering a therapeutically effective amount of the reconstituted nanoparticle composition to the subject, thereby treating the cancer.

In another aspect, provided herein is a method of making a nanoparticle complex, the method comprising mixing in vitro an aqueous carrier protein-therapeutic agent-paclitaxel nanoparticle with a binding agent under conditions to form the nanoparticle complex.

In another aspect, provided herein is a method of making a lyophilized nanoparticle composition comprising nanoparticle complexes, each of the nanoparticle complexes comprising a carrier protein, a binding agent with binding specificity for an anti-cancer epitope, and a therapeutically effective amount of a therapeutic agent and paclitaxel, the method comprising mixing in vitro an aqueous carrier protein-therapeutic agent-paclitaxel nanoparticle with a binding agent under conditions to form the nanoparticle complex, and lyophilizing the nanoparticle complexes to form the lyophilized nanoparticle composition, such that when reconstituted with an aqueous solution the nanoparticle complexes have binding specificity for the anti-cancer epitope.

In another aspect, provided herein is a method of making a lyophilized nanoparticle composition comprising nanoparticle complexes, each of the nanoparticle complexes comprising a carrier protein, a binding agent with binding specificity for an anti-cancer epitope, and a therapeutically effective amount of a therapeutic agent and paclitaxel derivative, wherein the paclitaxel derivative is less toxic than paclitaxel, the method comprising mixing in vitro an aqueous carrier protein-therapeutic agent-paclitaxel nanoparticle with a binding agent under conditions to form the nanoparticle complex, and lyophilizing the nanoparticle complexes to form the lyophilized nanoparticle composition, such that when reconstituted with an aqueous solution the nanoparticle complexes have binding specificity for the anti-cancer epitope.

These and other aspects described herein are set forth in more detail in the description below.

BRIEF DESCRIPTION OF THE DRAWINGS

FIG. 7 shows results of an in vivo efficacy study in MDA-MB-231 tumor xenograft in female athymic nude mice, where all nab-paclitaxel nanoparticles were prepared with non-toxic paclitaxel derivative.

DETAILED DESCRIPTION

Figure 1A:
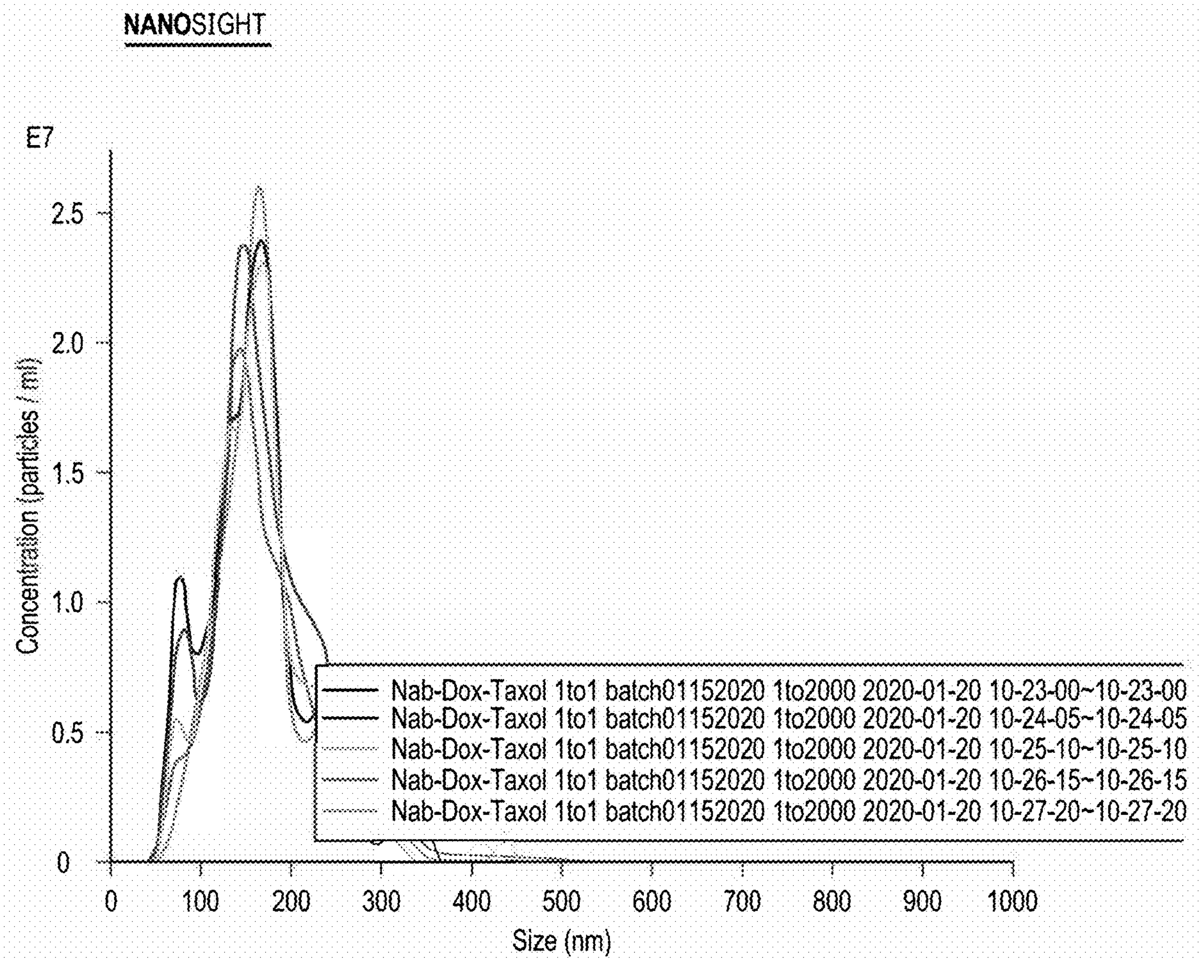
FIG. 1A shows the particle size of nanoparticles made with doxorubicin and paclitaxel in a 1:1, 1:3 and 1:9 ratio.
Figure 1A:
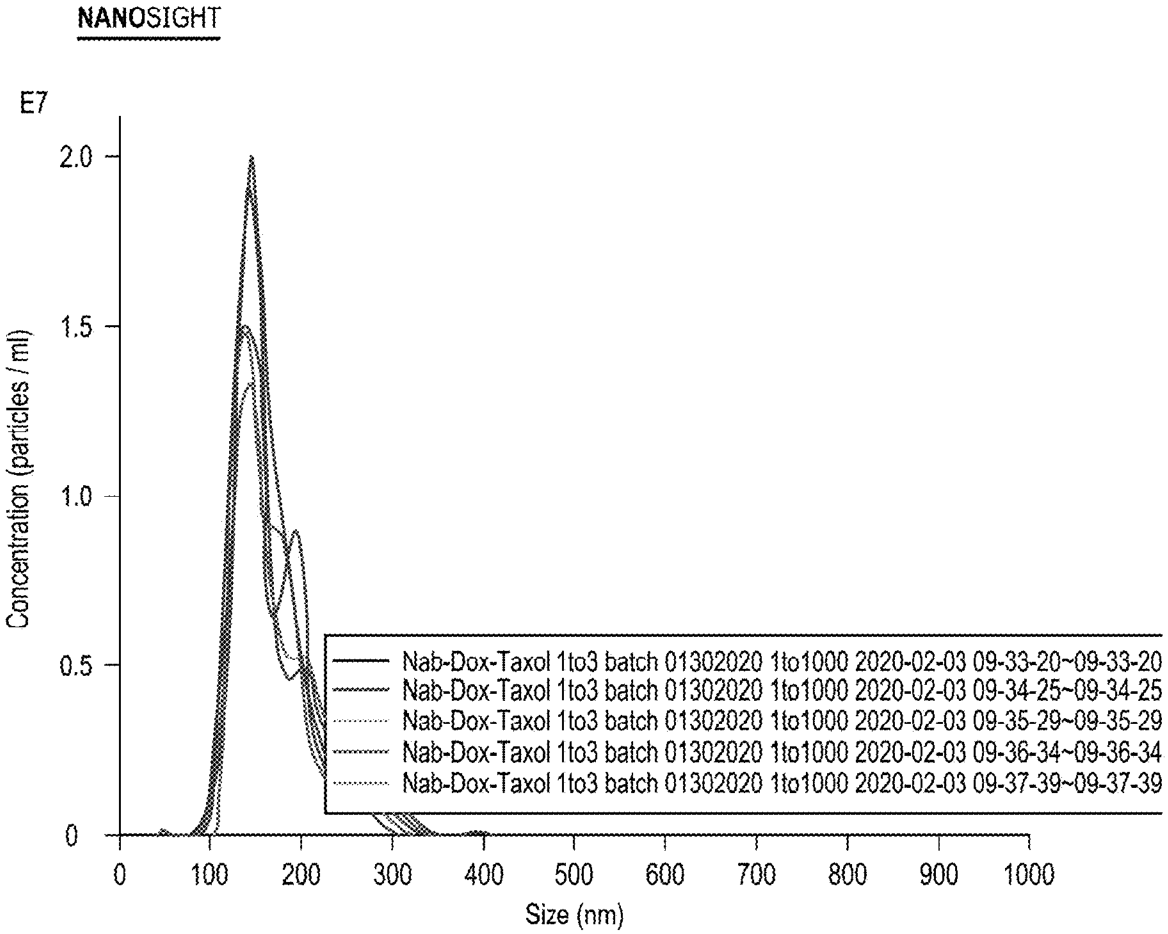
Figure 1A:
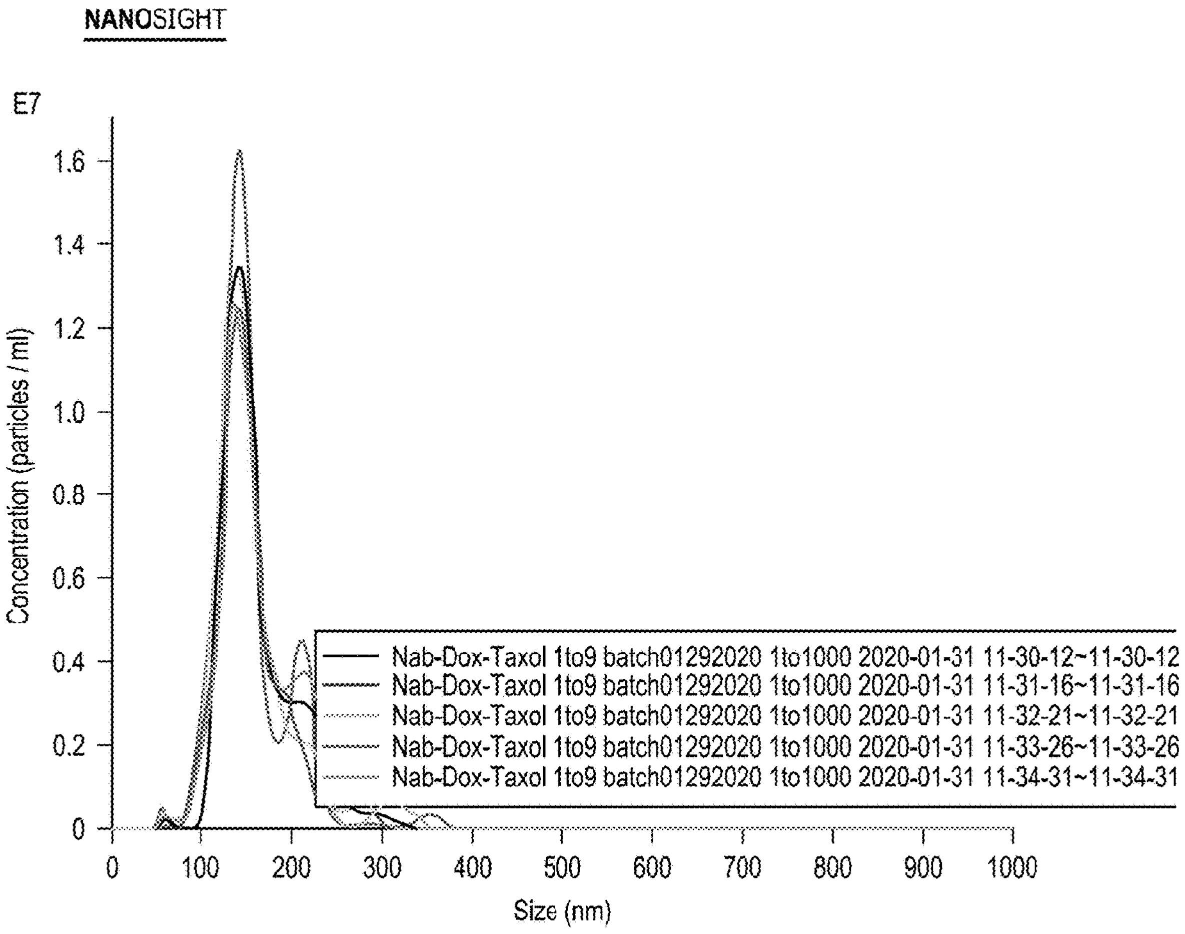

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features described herein can be used in any combination. Moreover, the present invention also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description herein is for the purpose of describing particular embodiments only and is not intended to be limiting.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three-letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together. The term "materially altered," as applied to polynucleotides described herein, refers to an increase or decrease in ability to express the encoded polypeptide of at least about 50% or more as compared to the expression level of a polynucleotide consisting of the recited sequence. The term "materially altered," as applied to polypeptides described herein, refers to an increase or decrease in biological activity of at least about 50% or more as compared to the activity of a polypeptide consisting of the recited sequence.

"Optional" or "optionally" means that the subsequently described event or circumstance can or cannot occur, and that the description includes instances where the event or circumstance occurs and instances where it does not.

As used herein, the term "sub-therapeutic" is used to describe an amount of a therapeutic agent (e.g., binding agent, e.g., antibody) that is below the amount of therapeutic agent conventionally used to treat a cancer. For example, a sub-therapeutic amount is an amount less than that defined by the manufacturer as being required for therapy.

The term "nanoparticle" as used herein refers to particles having at least one dimension which is less than 5 microns. In preferred embodiments, such as for intravenous administration, the nanoparticle is less than 1 micron. For direct administration, e.g., into a tumor, the nanoparticle can be larger. Even larger particles are expressly contemplated by the invention.

In a population of particles, the size of individual particles is distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50. Particle size may be determined by laser diffraction as is well known in the art, e.g., using a Mastersizer 2000 (available from Malvern Instruments Ltd, Worcestershire, UK) as described in WO 2016/057554.

The term "nanoparticle" may also encompass discrete multimers of smaller unit nanoparticles.

The terms "nab," "nab-paclitaxel," or "carrier protein-containing nanoparticles" as used herein, refer to albumin bound nanoparticles. Nab includes an albumin and a paclitaxel or an albumin and a paclitaxel derivative which form a nanoparticle where the paclitaxel or the paclitaxel derivative is non-covalently bound to the albumin. The nab may further include one or more therapeutic agents (e.g., doxorubicin or SN38).

Figure 3:
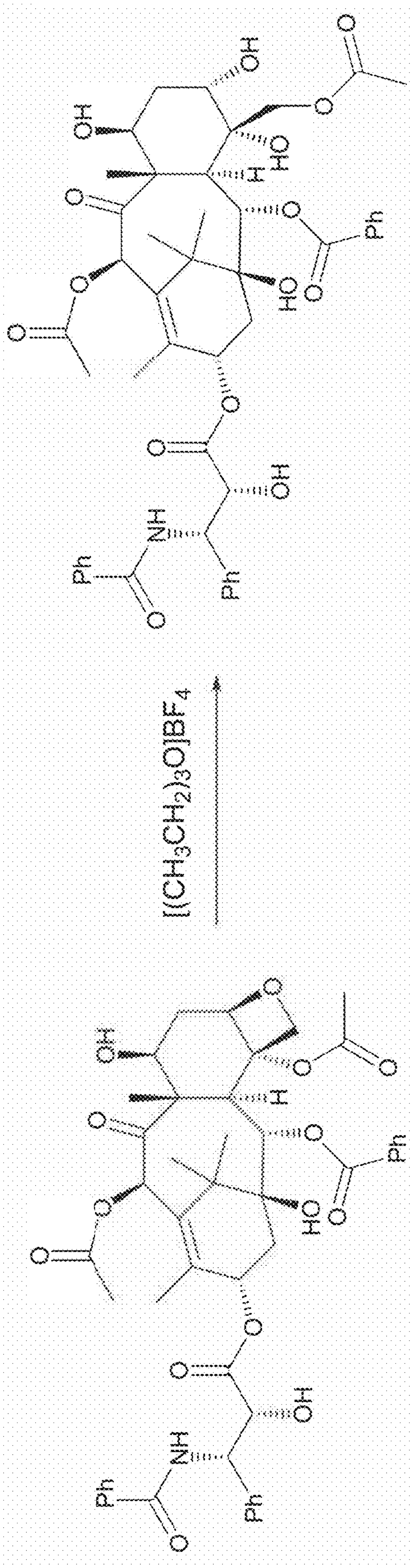
FIG. 3 shows the reaction of paclitaxel with Meerwein's Reagent to form Meerwein's product of paclitaxel (which is a non-toxic paclitaxel derivative).

The terms "paclitaxel derivative," "non-toxic paclitaxel (NTP)," or "non-toxic paclitaxel derivative" as used herein, refer to a paclitaxel derivative that is less toxic than paclitaxel. "less toxic than paclitaxel" refers to paclitaxel derivatives that exhibit reduced toxicity to (e.g., reduced killing of) cells, including cancer cells and normal cells, as compared to paclitaxel. For example, the Meerwein Product of Paclitaxel 20-acetoxy-4-deacetyl-5-epi-20, O-secotaxol (FIG. 3) has significantly reduced toxicity, likely due to breaking of the C-4, C-5 oxetane ring of paclitaxel.

The terms "NIC," "nanoparticle complex," or "carrier protein-containing nanoparticle/binding agent complex" as used herein, refer to a nano-immune conjugate comprising a carrier protein (e.g., albumin) and a paclitaxel or a paclitaxel derivative, binding agents (e.g., antibodies or antigen binding fragments thereof, aptamers, proteins, lectins), and optionally one or more therapeutic agent(s) (e.g., doxorubicin or SN38). Thus, NIC is composed of a "nab" non-covalently conjugated to binding agents (e.g., antibodies or antigen binding fragments thereof, aptamers, proteins, lectins), and optionally comprising one or more therapeutic agent(s).

The term "biosimilar" as used herein refers to a biopharmaceutical which is deemed to be comparable in quality, safety, and efficacy to a reference product marketed by an innovator company (Section 351(i) of the Public Health Service Act (42 U.S.C. 262(i)). A biosimilar is understood in the art to have the same primary amino acid sequence, and highly similar primary, secondary, tertiary, and quaternary structure, posttranslational modifications, and biological activities to its reference biologic (e.g., bevacizumab for bevacizumab biosimilars), wherein any minor differences have been verified to be clinically irrelevant such that clinical properties (functions, dosing, toxicity, etc.) of the biosimilar are the same as the reference biologic, as described in U.S. F.D.A. "Scientific considerations in demonstrating biosimilarity to a reference product: guidance for industry," 2015, incorporated herein by reference.

The term "carrier protein" as used herein refers to proteins that function to transport binding agents (e.g., antibodies) and/or other therapeutic agents (e.g., paclitaxel, SN38 and doxorubicin). The binding agents of the present disclosure can reversibly bind to the carrier proteins. Exemplary carrier proteins are discussed in more detail below.

The term "core" as used herein refers to central or inner portion of the nanoparticle which may be comprised of a carrier protein, a carrier protein and a therapeutic agent, or other agents or combination of agents. In some embodiments, a hydrophobic portion of the binding agent (e.g., the hydrophobic portion of an antibody) may be incorporated into the core.

As used herein, the term "enhancing the therapeutic outcome" and the like relative to a cancer patient refers to a slowing or diminution of the growth of cancer cells or a solid tumor, or a reduction in the total number of cancer cells or total tumor burden.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof. Examples of therapeutic agents that can be effectively employed in the disclosed methods include, but are not limited to, paclitaxel (TAXOL®), doxorubicin, and SN38.

As used herein, the term, "binding agent", "binding agent specific for", or "binding agent that specifically binds" refers to an agent that binds to a target antigen and does not significantly bind to unrelated compounds. Examples of binding agents that can be effectively employed in the disclosed methods include, but are not limited to, lectins, proteins, and antibodies, such as monoclonal antibodies, e.g., humanized monoclonal antibodies, chimeric antibodies, or polyclonal antibodies, or antigen-binding fragments thereof, as well as aptamers, Fc domain fusion proteins, and aptamers having or fused to a hydrophobic protein domain, e.g., Fc domain, etc. In some embodiments, the binding agent is an exogenous antibody. An exogenous antibody is an antibody not naturally produced in a mammal, e.g., in a human, by the mammalian immune system.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984); Harlow and Lane, Antibodies. A Laboratory Manual, Cold Spring Harbor Laboratory (1988); Hunkapiller and Hood, Nature, 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric.

The term "aptamer" refers to a nucleic acid molecule or peptide molecule that is capable of binding to a target molecule, such as a polypeptide. For example, target molecules to which an aptamer described herein may specifically bind to include, but are not limited to, CD20, CD38, CD52, PD-L1, Ly6E, HER2, HER3/EGFR DAF, ERBB-3 receptor, CSF-1R, STEAP1, CD3, CEA, CD40, OX40, Ang2-VEGF, and VEGF. The generation of aptamers with a particular binding specificity and the therapeutic use of aptamers are well established in the art. See, e.g., U.S. Pat. Nos. 5,475,096, 5,270,163, 5,582,981, 5,840,867, 6,011,020, 6,051,698, 6,147,204, 6,180,348 and 6,699,843, and the therapeutic efficacy of Macugen® (Eyetech, New York) for treating age-related macular degeneration.

Fc-fusion proteins are bioengineered polypeptides that join the crystallizable fragment (Fe) domain of an antibody with another biologically active agent, e.g., a protein domain, peptide, or nucleic acid or peptide aptamer to generate a molecule with desired structure-function properties and significant therapeutic potential. The gamma immunoglobulin (IgG) isotype is often used as the basis for generating Fc-fusion proteins because of favorable characteristics such as recruitment of effector function and increased plasma half-life. Given the range of aptamers, both peptide and nucleic acids, that can be used as fusion partners, Fc-fusion proteins have numerous biological and pharmaceutical applications.

The term "dissociation constant," also referred to as "Kd," refers to a quantity expressing the extent to which a particular substance separates into individual components (e.g., the protein carrier, binding agent, and optional therapeutic agent).

The terms "lyophilized," "lyophilization" and the like as used herein refer to a process by which the material (e.g., nanoparticles) to be dried is first frozen and then the ice or frozen solvent is removed by sublimation in a vacuum environment. An excipient is optionally included in pre-lyophilized formulations to enhance stability of the lyophilized product upon storage. In some embodiments, the nanoparticles can be formed from lyophilized components (carrier protein, binding agent and optional therapeutic) prior to use as a therapeutic. In other embodiments, the carrier protein, binding agent, and optional therapeutic agent are first combined into nanoparticles and then lyophilized. The lyophilized sample may further contain additional excipients.

The term "buffer" encompasses those agents which maintain the solution pH in an acceptable range prior to lyophilization and may include succinate (sodium or potassium), histidine, phosphate (sodium or potassium), Tris(tris(hydroxymethyl)aminomethane), diethanolamine, citrate (sodium) and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "bulking agents" comprises agents that provide the structure of the freeze-dried product. Common examples used for bulking agents include mannitol, glycine, lactose and sucrose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers.

The term "cryoprotectants" generally includes agents which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as sucrose, glucose, trehalose, and lactose; surfactants such as polysorbates; and amino acids such as glycine, arginine, and serine.

The term "lyoprotectant" includes agents that provide stability to the protein during the drying or 'dehydration' process (primary and secondary drying cycles), presumably by providing an amorphous glassy matrix and by binding with the protein through hydrogen bonding, replacing the water molecules that are removed during the drying process. This helps to maintain the protein conformation, minimize protein degradation during the lyophilization cycle and improve the long-term products. Examples include polyols or sugars such as sucrose and trehalose.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation into a solution.

A "stable" formulation is one in which the protein therein essentially retains its physical stability and/or chemical stability and/or biological activity upon storage.

The term "epitope" as used herein refers to the portion of an antigen which is recognized by a binding agent such as an antibody. Epitopes include, but are not limited to, a short amino acid sequence or peptide (optionally glycosylated or otherwise modified) enabling a specific interaction with a protein (e.g., an antibody) or ligand. For example, an epitope may be a part of a molecule to which the antigen-binding site of a binding agent attaches.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments "treating" or "treatment" refers to the killing of cancer cells.

The term "kill" with respect to a cancer treatment is directed to include any type of manipulation that will lead to the death of that cancer cell or at least a portion of a population of cancer cells.

The term "dose" refers to an amount of therapeutic agent given to a patient in need thereof. The attending clinician will select an appropriate dose from the range based on the patient's weight, age, health, stage of cancer, and other relevant factors, all of which are well within the skill of the art.

The term "unit dose" refers to a dose of an agent (e.g., therapeutic agent, binding agent, and/or nanoparticle complex) that is given to the patient to provide a desired result. In some instances, the unit dose is sold in a sub-therapeutic formulation (e.g., 10% of the therapeutic dose). The unit dose may be administered as a single dose or a series of subdoses. The therapeutic dose for an antibody for a given FDA-approved indication is recited in the prescribing information, for example the therapeutic dose of bevacizumab is 5 mg/kg to 15 mg/kg depending on the condition, and preferably a subtherapeutic dose ranges from 5% to 20% of the therapeutic dose. In such a preferred embodiment such a sub-therapeutic dose would range from 0.25 mg/kg to 3 mg/kg, more preferably from 0.5 to 2 mg/kg. The therapeutic dose for a binding agent (e.g., an antibody) for a given indication where the binding agent is not yet FDA approved or the binding agent is not yet approved for that indication, will be the amount that correlates to the therapeutic that has been approved for other indications, and thus the sub-therapeutic dose for the non-FDA approved indications is readily calculated as a percent of the therapeutic dose (e.g., 10% of the therapeutic dose). For example, the therapeutic dose and therefore the sub-therapeutic dose of an antibody for the treatment of metastatic melanoma correlates to the therapeutic dose for metastatic cancers in general that has been approved.

Additionally, some terms used in this specification are more specifically defined below.

Overview

The current invention is predicated, in part, on the surprising discovery that treatment of a cancer in a patient with albumin-bound therapeutic agent/paclitaxel or paclitaxel derivative/anti-cancer antibody nanoparticle complexes provides for unexpectedly improved therapeutic outcomes (therapeutic agent such as doxorubicin or SN38). This document provides methods and materials involved in treating cancer. For example, this document provides methods and materials for using complexes containing carrier protein-containing nanoparticles (e.g., albumin-bound therapeutic agent (e.g., doxorubicin or SN38)/paclitaxel or paclitaxel derivative nanoparticles) and binding agents (e.g., Fe-fusion proteins, e.g., aptamers, e.g., antibodies, e.g., anti-cancer antibodies) to treat cancer.

The methods and materials provided herein can be used to treat any type of cancer. For example, the methods and materials provided herein can be used to treat skin cancer (e.g., melanoma) and breast cancer. In some cases, the methods and materials provided herein can be used to treat cancer in any type of mammal including, without limitation, mice, rats, dogs, cats, horses, cows, pigs, monkeys, and humans. When treating skin cancer, any type of skin cancer, such as melanoma, can be treated using the methods and materials provided herein. For example, stage I, stage II, stage III, or stage IV melanoma can be treated. In some cases, a lymph node positive, a lymph node negative, or a metastatic melanoma can be treated as described herein.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; renal cancer including adenocarcinoma and Wilms tumor; and those cancers listed in Table 1 and Table 2.

Carrier protein-bound chemotherapeutic/binding agent complexes (e.g., antibody-complexed albumin-bound doxorubicin/paclitaxel nanoparticle complexes, antibody-complexed albumin-bound doxorubicin/paclitaxel derivative nanoparticle complexes, antibody-complexed albumin-bound SN38/paclitaxel nanoparticle complexes, and antibody-complexed albumin-bound SN38/paclitaxel derivative nanoparticle complexes) and methods of preparing the nanoparticle complexes are described, for example, in PCT Patent Publication Nos. WO 2012/154861, WO 2014/055415, WO 2015/191969, WO 2015/195476, WO 2016/057554, WO 2017/031368, WO 2017/176265, WO 2018/048816, and WO 2018/048958, the disclosures of which are incorporated herein by reference in their entirety.

In some embodiments, the antibody is a biosimilar version thereof. In some embodiments, the antibodies are a substantially single layer of antibodies on all or part of the surface of the nanoparticle.

Binding Agents

In some embodiments, the binding agent may be an Fc-fusion protein and/or an aptamer. In some embodiments, the binding agent may be an antibody (e.g., an anti-cancer antibody) or an antigen-binding fragment thereof. In some embodiments, the antibody may be selected from the antibodies listed in Table 1. In embodiments, the antibody is an anti-PDL1 H6B1L-EM antibody (STI3031) HC/LC SEQ ID NO. 1/SEQ ID NO. 2 (disclosed in PCT Patent Publication No. WO 2017/132562 as SEQ ID NO. 1/SEQ ID NO. 2 (H6B1L-EM)). The antibody may be a biosimilar version thereof. Biosimilars of antibodies in Table 1 include, but are not limited to, bevacizumab-awwb ("MVASI™") as a biosimilar of bevacizumab, GP2013 and rituximab-abbs ("TRUXIMA®") as biosimilars of rituximab, trastuzumab-dkst ("OGIVRI"), trastuzumab-dttb ("ONTRUZANT®"), and trastuzumab-pkrb ("HERZUMA®") as biosimilars of trastuzumab.

TABLE 1

| Antibodies | | |
|---|---|---|
| Antibody | Antigen | Disease Indications |
| cetuximab | EGFR | head and neck cancer; colon cancer; colorectal cancer; non-small cell lung cancer cervical cancer, glioblastoma, renal cell cancer, ovarian epithelial, fallopian tube or primary peritoneal cancer |

TABLE 1-continued

| Antibodies | | |
|---|---|---|
| Antibody | Antigen | Disease Indications |
| trastuzumab | HER2 | breast cancer; stomach cancer; adenocarcinoma |
| panitumumab | EGFR | colon cancer; colorectal carcinoma |
| bevacizumab | VEGF | colon cancer, ovarian cancer; lung cancer; renal cell carcinoma; glioblastoma multiforme, fallopian tube cancer, primary peritoneal cancer; cervical cancer; colorectal cancer |
| ofatumumab | CD20 | CLL/lymphoma |
| alemtuzumab | CD52 | CLL/lymphoma |
| rituximab | CD20 | leukemia (AML, ANLL, ALL), lymphoma, follicular lymphoma, diffuse large B cell lymphoma, CLL; non-Hodgkin's lymphoma |
| daratumumab | CD38 | multiple myeloma |
| SAR650984 | CD38 | multiple myeloma |
| MOR202 | CD38 | multiple myeloma |
| atezolizumab | PD-L1 | urothelial carcinoma; metastatic non-small cell lung cancer; urothelial carcinoma |
| avelumab | PD-L1 | metastatic merkel cell carcinoma; urothelial carcinoma |
| blinatumomab | CD19/CD3 bispecific | precursor B-cell acute lymphoblastic leukemia; ALL; R/R ALL |
| dinutuximab | GD2 | neuroblastoma |
| durvalumab | PD-L1 | urothelial carcinoma; non-small cell lung cancer |
| denosumab | RANKL | bone metastases; multiple myeloma; giant cell tumor of bone; prostate cancer or breast cancer inpatients receiving androgen deprivation or adjuvant aromatase inhibitor therapy (ADT or AI) |
| elotuzumab | SLAMF7 | multiple myeloma |
| ipilimumab | CTLA4 | metastatic melanoma; melanoma; renal cell carcinoma; metastatic colorectal cancer (MSI-H or dMMR, with nivolumab) |
| necitumumab | EGFR | metastatic squamous non-small cell lung carcinoma |
| nivolumab | PD-1 | melanoma; metastatic melanoma; metastatic squamous non-small cell lung cancer; renal cell carcinoma; metastatic small cell lung cancer; metastatic colorectal cancer (MSI-H or dMMR); hepatocellular carcinoma; urothelial carcinoma; SCCHM (squamous cell carcinoma of the head and neck); Hodgkin's lymphoma |
| obinutuzumab | CD20 | CLL; diffuse large B-cell lymphoma (DLBCL); NHL; follicular lymphoma (FL) |
| ocrelizumab | CD20 | multiple sclerosis |
| olaratumab | PDGFRA | soft tissue sarcoma |
| pembrolizumab | PD-1 | melanoma; non-small cell lung cancer; cervical cancer; hepatocellular carcinoma; urothelial cancer; primary mediastinal B-cell lymphoma (PMBCL); PDl1+ metastatic, gastric, or gastroesophageal junction adenocarcinoma; Hodgkin's lymphoma; HNSCC (head and neck squamous cell carcinoma) |
| ramucirumab | VEGFR2 | gastric cancer; colorectal cancer; NSCLC; GEJ adenocarcinoma (gastric or gastroesophageal junction) |
| ranibizumab | VEGFR1/2 | macular degeneration |
| istiratumab | IGFR1/HER3(ErbB3) bispecific | pancreatic cancer |
| lilotomab | CD37 | non-Hodgkin's lymphoma |
| moxetumomab | CD22 | refractory hairy cell leukemia (HCL) and acute lymphoblastic leukemia (ALL) |
| pemtumomab | MUC1 | ovarian cancer, peritoneal cancer |
| 3F8 | GD2 | neuroblastoma |
| tositumomab | CD20 | non-Hodgkin's lymphoma |
| racotumomab | NGNA ganglioside | non-small cell lung cancer |
| bemarituzumab | FGFR2 | gastroesophageal adenocarcinoma |
| cirmtuzumab | ROR1 | CLL |
| oportuzumab | EpCAM | bladder cancer |
| pertuzumab | HER2 | breast cancer |
| polatuzumab | CD79b | non-Hodgkin's lymphoma; large B-cell lymphoma |

TABLE 1-continued

| Antibodies | | |
|---|---|---|
| Antibody | Antigen | Disease Indications |
| rovalpituzumab | DLL3 | small-cell lung cancer |
| sacituzumab | Trop-2 | small cell lung cancer, pancreatic cancer, breast cancer |
| pankomab | TA-MUC1 | ovarian cancer |
| catumaxomab | CD3/EpCAM bispecific | cancer-related malignant ascites |
| duligotuzumab | HER3/EGFR(HER1) bispecific | solid tumors |
| brentuximab | CD30 | anaplastic large cell lymphoma, T cell lymphomas; Hodgkin lymphoma |
| cemiplimab-rwlc | PD-1 | cutaneous squamous cell carcinoma |
| mogamulizumab-kpkc | CCR4 | Sezary syndrome, mycosis fungoides, T cell lymphoma, |
| gemtuzumab | CD33 | CD33+ AML |
| inotuzumab | CD22 | ALL |
| bevacizumab-awwb/mvasi | VEGF | colon cancer, ovarian cancer; lung cancer; renal cell carcinoma; glioblastoma multiforme, fallopian tube cancer, primary peritoneal cancer; cervical cancer; colorectal cancer |
| CT-P10/rituximab-abbs/truxima | CD20 | leukemia (AML, ANLL, ALL), lymphoma, follicular lymphoma, diffuse large B cell lymphoma, CLL; non-Hodgkin's lymphoma |
| trastuzumab-dkst/ogivri | HER2 | breast cancer; stomach cancer; adenocarcinoma |
| trastuzumab-dttb/ontruzant | HER2 | breast cancer; stomach cancer; adenocarcinoma |
| trastuzumab-pkrb/herzuma | HER2 | breast cancer; stomach cancer; adenocarcinoma |
| GP2013/rixathon | CD20 | leukemia (AML, ANLL, ALL), lymphoma, follicular lymphoma, diffuse large B cell lymphoma, CLL; non-Hodgkin's lymphoma |
| ibritumomab | CD20 | non-Hodgkin's lymphoma |
| lifastuzumab | SLC34A2 | ovarian cancer |

In some embodiments, the carrier protein can be albumin, gelatin, elastin (including topoelastin) or elastin-derived polypeptides (e.g., α-elastin and elastin-like polypeptides (ELPs)), gliadin, legumin, zein, soy protein (e.g., soy protein isolate (SPI)), milk protein (e.g., β-lactoglobulin (BLG) and casein), or whey protein (e.g., whey protein concentrates (WPC) and whey protein isolates (WPI)). In some embodiments, the carrier protein is albumin. In some embodiments, the albumin is egg white (ovalbumin), bovine serum albumin (BSA), or the like. In some embodiments, the carrier protein is human serum albumin (HSA), e.g., recombinant HSA. In some embodiments, the carrier protein is a generally regarded as safe (GRAS) excipient approved by the United States Food and Drug Administration (FDA).

Therapeutic Agents

Nanoparticles comparing doxorubicin and paclitaxel as therapeutic agents were developed. The combination of agents provides substantial benefits over nanoparticles comprising paclitaxel alone, including increased stability and increase cytotoxicity. Nanoparticles comparing SN38 (an active metabolite of irinotecan), and paclitaxel as therapeutic agents were also developed. The combination of agents provides substantial benefits over nanoparticles comprising paclitaxel alone, including increased in cytotoxicity in vitro and in vivo. Thus, the nanoparticle complexes described herein comprise at least doxorubicin or SN38, and paclitaxel (or a paclitaxel derivative) as therapeutic agents. The nanoparticle complexes may include additional therapeutic agents.

It is understood that the therapeutic agent(s) may be located inside the nanoparticle, on the outside surface of the nanoparticle, or both. In some embodiments, the nanoparticle complex may contain more than one therapeutic agent, for example, two therapeutic agents, three therapeutic agents, four therapeutic agents, five therapeutic agents, or more. Furthermore, a nanoparticle complex may contain the same or different therapeutic agents inside and outside the nanoparticle. In some embodiments, any carrier protein, binding agent, therapeutic agent, or any combination thereof is expressly excluded. For example, in some embodiments, a composition may comprise any carrier protein and therapeutic except ABRAXANE® and/or any targeting antibody except bevacizumab.

In some embodiments, the additional therapeutic agent is selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, cyclophosphamide, bendamustine, bortezomib, cabazitaxel, chlorambucil, dasatinib, docetaxel, epirubicin, erlotinib, idarubicin, hydroxyurea, imatinib, adriamycin, prednisone, dexamethasone, cytarabine, thiotepa, ifosfamide, dacarbazine, bleomycin, ibrutinib, campath-B, gemcitabine, revlimid, sirolimus, temsirolimus, bexxar, brentuximab, bendamustine, vedotin, emtansine, and/or those listed in Table 2.

TABLE 2

| Cancer therapeutic agents | |
|---|---|
| Drug | Target(s) |
| Abitrexate (Methotrexate) | Acute lymphoblastic leukemia; breast cancer; gestational trophoblastic disease, head and neck cancer; lung cancer; mycosis fungoides; non-Hodgkin lymphoma osteosarcoma |
| ABRAXANE ® (Paclitaxel Albumin-stabilized Nanoparticle Formulation) | Breast cancer; non-small cell lung cancer; pancreatic cancer |
| ABVD (Adriamycin, bleomycin, vinblastine sulfate, dacarbazine) | Hodgkin lymphoma |
| ABVE (Adriamycin, bleomycin, vincristine sulfate, etoposide) | Hodgkin lymphoma |
| ABVE-PC (Adriamycin, bleomycin, vincristine sulfate, etoposide, prednisone, cyclophosphamide) | Hodgkin lymphoma |
| AC (Adriamycin cyclophosphamide) | Breast cancer |
| AC-T (Adriamycin, cyclophosphamide, Taxol) | Breast cancer |
| Adcetris (Brentuximab Vedotin) | Anaplastic large cell lymphoma; Hodgkin lymphoma |
| ADE (Cytarabine (Ara-C), Daunorubicin Hydrochloride, Etoposide) | Acute myeloid leukemia |
| Ado-Trastuzumab Emtansine | Breast cancer |
| Adriamycin (Doxorubicin Hydrochloride) | Acute lymphoblastic leukemia; acute myeloid leukemia; breast cancer, gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor |
| Adrucil (Fluorouracil) | Basal cell carcinoma; breast cancer; colorectal cancer; gastric (stomach) adenocarcinoma; pancreatic cancer; squamous cell carcinoma of the head and neck |
| Afatinib Dimaleate | Non-small cell lung cancer |
| Afinitor (Everolimus) | Breast cancer, pancreatic cancer; renal cell carcinoma; subependymal giant cell astrocytoma |
| Alimta (Pemetrexed Disodium) | Malignant pleural mesothelioma; non-small cell lung cancer |
| Ambochlorin (Chlorambucil) | Chronic lymphocytic leukemia; Hodgkin lymphoma; non-Hodgkin lymphoma |
| Anastrozole | Breast cancer |
| Aredia (Pamidronate Disodium) | Breast cancer; multiple myeloma |
| Arimidex (Anastrozole) | Breast cancer |
| Aromasin (Exemestane) | Advanced breast cancer; early-stage breast cancer and estrogen receptor positive |
| Arranon (Nelarabine) | T-cell acute lymphoblastic leukemia; T-cell lymphoblastic lymphoma |
| Azacitidine | Myelodysplastic syndromes |
| BEACOPP | Hodgkin lymphoma |
| Becenum (Carmustine) | Brain tumors; Hodgkin lymphoma; multiple myeloma; non-Hodgkin lymphoma |
| Beleodaq (Belinostat) | Peripheral T-cell lymphoma |
| BEP | Ovarian germ cell tumors; testicular germ cell tumors |
| Bicalutamide | Prostate cancer |
| BiCNU (Carmustine) | Brain tumors; Hodgkin lymphoma; multiple myeloma; non-Hodgkin lymphoma |
| Bleomycin | Hodgkin lymphoma; non-Hodgkin lymphoma; penile cancer; squamous cell carcinoma of the cervix; squamous cell carcinoma of the head and neck; squamous cell carcinoma of the vulva; testicular cancer |
| Bosulif (Bosutinib) | Chronic myelogenous leukemia |
| Brentuximab Vedotin | Anaplastic large cell lymphoma; Hodgkin lymphoma |
| Busulfan | Chronic myelogenous leukemia |
| Busulfex (Busulfan) | Chronic myelogenous leukemia |
| Cabozantinib-S-Malate | Medullary thyroid cancer |
| CAF | Breast cancer |
| Camptosar (Irinotecan Hydrochloride) | Colorectal cancer |
| CAPOX | Colorectal cancer |
| Carfilzomib | Multiple myeloma |

TABLE 2-continued

| Cancer therapeutic agents | |
|---|---|
| Drug | Target(s) |
| Casodex (Bicalutamide) | Prostate cancer |
| CeeNU (Lomustine) | Brain tumors; Hodgkin lymphoma |
| Ceritinib | Non-small cell lung cancer |
| Cerubidine (Daunorubicin Hydrochloride) | Acute lymphoblastic leukemia; acute myeloid leukemia |
| Chlorambucil | Chronic lymphocytic leukemia; Hodgkin lymphoma; non-Hodgkin lymphoma |
| CHLORAMBUCIL-PREDNISONE | Chronic lymphocytic leukemia |
| CHOP | Non-Hodgkin lymphoma |
| Cisplatin | Bladder cancer; cervical cancer; malignant mesothelioma; non-small cell lung cancer; ovarian cancer; squamous cell carcinoma of the head and neck; testicular cancer |
| Clafen (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non- Hodgkin lymphoma; ovarian cancer; retinoblastoma |
| Clofarex (Clofarabine) | Acute lymphoblastic leukemia |
| CMF | Breast cancer |
| Cometriq ( Cabozantinib-S-Malate) | Medullary thyroid cancer |
| COPP | Hodgkin lymphoma; non-Hodgkin lymphoma |
| COPP-ABV | Hodgkin lymphoma |
| Cosmegen (Dactinomycin) | Ewing sarcoma; gestational trophoblastic disease; rhabdomyosarcoma; solid tumors; testicular cancer; Wilms tumor |
| CVP | Non-Hodgkin lymphoma; chronic lymphocytic leukemia |
| Cyclophosphamide | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non- Hodgkin lymphoma; ovarian cancer; retinoblastoma. |
| Cyfos (Ifosfamide) | Testicular germ cell tumors |
| Cyramza (Ramucirumab) | Adenocarcinoma; colorectal cancer; non-small cell lung cancer |
| Cytarabine | Acute lymphoblastic leukemia; acute myeloid leukemia; chronic myelogenous leukemia; meningeal leukemia |
| Cytosar-U (Cytarabine) | Acute lymphoblastic leukemia; acute myeloid leukemia; chronic myelogenous leukemia; meningeal leukemia |
| Cytoxan (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non- Hodgkin lymphoma; ovarian cancer; retinoblastoma |
| Dacarbazine | Hodgkin lymphoma; melanoma |
| Dacogen (Decitabine) | Myelodysplastic syndromes |
| Dactinomycin | Ewing sarcoma; gestational trophoblastic disease; rhabdomyosarcoma; solid tumors; testicular cancer; Wilms tumor |
| Daunorubicin Hydrochloride | Acute lymphoblastic leukemia; acute myeloid leukemia |
| Degarelix | Prostate cancer |
| Denileukin Diftitox | Cutaneous T-cell lymphoma |
| DepoCyt (Liposomal Cytarabine) | Lymphomatous meningitis |
| DepoFoam (Liposomal Cytarabine) | Lymphomatous meningitis |
| Docetaxel | Breast cancer; adenocarcinoma of the stomach or gastroesophageal junction; non-small cell lung cancer; prostate cancer; squamous cell carcinoma of the head and neck |

TABLE 2-continued

Cancer therapeutic agents

| Drug | Target(s) |
|---|---|
| Doxil (Doxorubicin Hydrochloride Liposome) | AIDS-related Kaposi sarcoma; multiple myeloma; ovarian cancer |
| Doxorubicin Hydrochloride | Acute lymphoblastic leukemia; acute myeloid leukemia; breast cancer; gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor. |
| Dox-SL (Doxorubicin Hydrochloride Liposome) | AIDS-related Kaposi sarcoma; multiple myeloma; ovarian cancer |
| DTIC-Dome (Dacarbazine) | Hodgkin lymphoma; melanoma |
| Efudex (Fluorouracil) | Basal cell carcinoma; breast cancer; colorectal cancer; gastric (stomach) adenocarcinoma; pancreatic cancer; squamous cell carcinoma of the head and neck |
| Ellence (Epirubicin Hydrochloride) | Breast cancer |
| Eloxatin (Oxaliplatin) | Colorectal cancer; stage III colon cancer |
| Emend (Aprepitant) | Nausea and vomiting caused by chemotherapy and nausea and vomiting after surgery |
| Enzalutamide | Prostate cancer |
| Epirubicin Hydrochloride | Breast cancer |
| EPOCH | Non-Hodgkin lymphoma |
| Eribulin Mesylate | Breast cancer |
| Erivedge (Vismodegib) | Basal cell carcinoma |
| Erlotinib Hydrochloride | Non-small cell lung cancer; pancreatic cancer |
| Erwinaze (Asparaginase *Erwinia chrysanthemi*) | Acute lymphoblastic leukemia |
| Etopophos (Etoposide Phosphate) | Small cell lung cancer; testicular cancer |
| Evacet (Doxorubicin Hydrochloride Liposome) | AIDS-related Kaposi sarcoma; multiple myeloma; ovarian cancer |
| Everolimus | Breast cancer; pancreatic cancer; renal cell carcinoma; subependymal giant cell astrocytoma |
| Evista (Raloxifene Hydrochloride) | Breast cancer |
| Exemestane | Breast cancer |
| Fareston (Toremifene) | Breast cancer |
| Farydak (Panobinostat) | Multiple myeloma |
| Faslodex (Fulvestrant) | Breast cancer |
| FEC | Breast cancer |
| Femara (Letrozole) | Breast cancer |
| Filgrastim | Neutropenia |
| Fludara (Fludarabine Phosphate) | Chronic lymphocytic leukemia |
| Fluoroplex (Fluorouracil) | Basal cell carcinoma; breast cancer; colorectal cancer; gastric (stomach) adenocarcinoma; pancreatic cancer; squamous cell carcinoma of the head and neck |
| Folex (Methotrexate) | Acute lymphoblastic leukemia; breast cancer; gestational trophoblastic disease; head and neck cancer; lung cancer; mycosis fungoides; non-Hodgkin lymphoma; osteosarcoma |
| FOLFIRI | Colorectal cancer |
| FOLFIRI-BEVACIZUMAB | Colorectal cancer |
| FOLFIRI-CETUXIMAB | Colorectal cancer |
| FOLFIRINOX | Pancreatic cancer |
| FOLFOX | Colorectal cancer |
| Folotyn (Pralatrexate) | Peripheral T-cell lymphoma |
| FU-LV | Colorectal cancer; esophageal cancer; gastric cancer |
| Fulvestrant | Breast cancer |
| Gefitinib | Non-small cell lung cancer |
| Gemcitabine Hydrochloride | Breast cancer; non-small cell lung cancer; ovarian cancer; pancreatic cancer |
| GEMCITABINE-CISPLATIN | Biliary tract cancer; bladder cancer; cervical cancer; malignant mesothelioma; non-small cell lung cancer; ovarian cancer; pancreatic cancer |
| GEMCITABINE-OXALIPLATIN | Pancreatic cancer |
| Gemtuzumab Ozogamicin (antibody drug conjugate) | Acute myeloid leukemia |
| Gemzar (Gemcitabine Hydrochloride) | Breast cancer; non-small cell lung cancer; ovarian cancer; pancreatic cancer |
| Gilotrif (Afatinib Dimaleate) | Non-small cell lung cancer |
| Gleevec (Imatinib Mesylate) | Acute lymphoblastic leukemia; chronic eosinophilic leukemia or hypereosinophilic syndrome; chronic myelogenous leukemia; dermatofibrosarcoma protuberans; gastrointestinal stromal tumor; myelodysplastic/myeloproliferative neoplasms; systemic mastocytosis. |

TABLE 2-continued

| Cancer therapeutic agents | |
|---|---|
| Drug | Target(s) |
| Gliadel (Carmustine Implant) | Glioblastoma multiforme; malignant glioma |
| Goserelin Acetate | Breast cancer; prostate cancer |
| Halaven (Eribulin Mesylate) | Breast cancer |
| Hycamtin (Topotecan Hydrochloride) | Cervical cancer; ovarian cancer; small cell lung cancer |
| Hyper-CVAD | Acute lymphoblastic leukemia; non-Hodgkin lymphoma |
| Ibrance (Palbociclib) | Breast cancer |
| Ibrutinib | Chronic lymphocytic leukemia; mantel cell lymphoma; |
| ICE | Hodgkin lymphoma; non-Hodgkin lymphoma |
| Iclusig (Ponatinib Hydrochloride) | Acute lymphoblastic leukemia; Chronic myelogenous leukemia |
| Idamycin (Idarubicin Hydrochloride) | Acute myeloid leukemia |
| Imatinib Mesylate | Acute lymphoblastic leukemia; chronic eosinophilic leukemia or hypereosinophilic syndrome; chronic myelogenous leukemia; dermatofibrosarcoma protuberans; gastrointestinal stromal tumor; myelodysplastic/myeloproliferative neoplasms; systemic mastocytosis. |
| Imbruvica (Ibrutinib) | Chronic lymphocytic leukemia; mantle cell lymphoma; Waldenstr6m macroglo bulinemia |
| Inlyta (Axitinib) | Renal cell carcinoma |
| Iressa (Gefitinib) | Non-small cell lung cancer; |
| Irinotecan Hydrochloride (SN38 active metabolite of irinotecan) | Colorectal cancer; Non-small cell lung cancer |
| Istodax (Romidepsin) | Cutaneous T-cell lymphoma |
| Ixempra (Ixabepilone) | Breast cancer |
| Jevtana (Cabazitaxel) | Prostate cancer |
| Keoxifene (Raloxifene Hydrochloride) | Breast cancer |
| Kyprolis (Carfilzomib) | Multiple myeloma |
| Lenvima (Lenvatinib Mesylate) | Thyroid cancer |
| Letrozole | Breast cancer |
| Leucovorin Calcium | Colorectal cancer |
| Leukeran (Chlorambucil) | Chronic lymphocytic leukemia; Hodgkin lymphoma; non-Hodgkin lymphoma |
| Leuprolide Acetate | Prostate cancer |
| Linfolizin (Chlorambucil) | Chronic lymphocytic leukemia; Hodgkin lymphoma; non-Hodgkin lymphoma |
| LipoDox (Doxorubicin Hydrochloride Liposome) | AIDS-related Kaposi sarcoma; multiple myeloma; ovarian cancer |
| Lomustine | Brain tumors; Hodgkin lymphoma |
| Lupron (Leuprolide Acetate) | Prostate cancer |
| Lynparza (Olaparib) | Ovarian cancer |
| Marqibo (Vincristine Sulfate Liposome) | Acute lymphoblastic leukemia |
| Matulane (Procarbazine Hydrochloride) | Hodgkin lymphoma |
| Mechlorethamine Hydrochloride | Bronchogenic carcinoma; chronic lymphocytic leukemia; chronic myelogenous leukemia; Hodgkin lymphoma; malignant pleural effusion, malignant pericardial effusion, and malignant peritoneal effusion; mycosis fungoides; non-Hodgkin lymphoma |
| Megace (Megestrol Acetate) | Breast cancer; endometrial cancer |
| Mekinist (Trametinib) | Melanoma |
| Mercaptopurine | Acute lymphoblastic leukemia |
| Mesnex (Mesna) | Hemorrhagic cystitis |
| Methazolastone (Temozolomide) | Anaplastic astrocytoma; glioblastoma multiforme |
| Mexate (Methotrexate) | Acute lymphoblastic leukemia; breast cancer; gestational trophoblastic disease; head and neck cancer; lung cancer; mycosis fungoides; non-Hodgkin lymphoma; osteosarcoma |
| Mexate-AQ (Methotrexate) | Acute lymphoblastic leukemia; breast cancer; gestational trophoblastic disease; head and neck cancer; lung cancer; mycosis fungoides; non-Hodgkin lymphoma; osteosarcoma |
| Mitoxantrone Hydrochloride | Acute myeloid leukemia; prostate cancer |
| Mitozytrex (Mitomycin C) | Gastric (stomach) and pancreatic adenocarcinoma |
| MOPP | Hodgkin lymphoma |
| Mozobil (Plerixafor) | Multiple myeloma; non-Hodgkin lymphoma |
| Mustargen (Mechlorethamine Hydrochloride) | Bronchogenic carcinoma; chronic lymphocytic leukemia; chronic myelogenous leukemia; Hodgkin lymphoma; malignant pleural effusion, malignant pericardial effusion, and malignant peritoneal effusion; mycosis |

TABLE 2-continued

| Cancer therapeutic agents | |
|---|---|
| **Drug** | **Target(s)** |
| | fungoides; non-Hodgkin lymphoma |
| Myleran (Busulfan) | Chronic myelogenous leukemia |
| Mylotarg (Gemtuzumab Ozogamicin) | Acute myeloid leukemia |
| Nanoparticle Paclitaxel (Paclitaxel Albumin- stabilized Nanoparticle Formulation) | Breast cancer; Non-small cell lung cancer; Pancreatic cancer |
| Navelbine (Vinorelbine Tartrate) | Non-small cell lung cancer |
| Nelarabine | T-cell acute lymphoblastic leukemia |
| Neosar (Cyclophosphamide) | Acute lymphoblastic leukemia; Acute myeloid leukemia; Breast cancer; Chronic lymphocytic leukemia; Chronic myelogenous leukemia; Hodgkin lymphoma; Multiple myeloma; Mycosis fungoides; Neuroblastoma; Non- Hodgkin lymphoma; Ovarian cancer; Retinoblastoma |
| Nexavar (Sorafenib Tosylate) | Hepatocellular carcinoma; Renal cell carcinoma; Thyroid cancer |
| Nilotinib | Chronic myelogenous leukemia |
| Nolvadex (Tamoxifen Citrate) | Breast cancer |
| Odomzo (Sonidegib) | Basal cell carcinoma |
| OEPA | Hodgkin lymphoma |
| OFF | Pancreatic cancer |
| Olaparib | Ovarian cancer |
| Oncaspar (Pegaspargase) | Acute lymphoblastic leukemia |
| OPPA | Hodgkin lymphoma |
| Oxaliplatin | Colorectal cancer; Stage III colon cancer |
| Paclitaxel | AIDS-related Kaposi sarcoma; Breast cancer; Non-small cell lung cancer; Ovarian cancer |
| Paclitaxel Albumin-stabilized Nanoparticle Formulation | Breast cancer; Non-small lung cancer; Pancreatic cancer |
| PAD | Multiple myeloma |
| Palbociclib | Breast cancer |
| Pamidronate Disodium | Breast cancer; Multiple myeloma |
| Panobinostat | Multiple myeloma |
| Paraplat (Carboplatin) | Non-small cell lung cancer; Ovarian cancer |
| Paraplatin (Carboplatin) | Non-small cell lung cancer; Ovarian cancer |
| Pazopanib Hydrochloride | Renal cell carcinoma; Soft tissue sarcoma |
| Pegaspargase | Acute lymphoblastic leukemia |
| Pemetrexed Disodium | Malignant pleural mesothelioma; Non-small cell lung cancer |
| Platinol (Cisplatin) | Bladder cancer; Cervical cancer; Malignant mesothelioma; Non-small cell lung cancer; Ovarian cancer; Squamous cell carcinoma of the head and neck; Testicular cancer |
| Platinal-AQ (Cisplatin) | Bladder cancer; Cervical cancer; Malignant mesothelioma; Non-small cell lung cancer; Ovarian cancer; Squamous cell carcinoma of the head and neck; Testicular cancer |
| Plerixafor | Multiple myeloma; Non-Hodgkin lymphoma |
| Pomalidomide | Multiple myeloma |
| Pomalyst (Pomalidomide) | Multiple myeloma |
| Pontinib Hydrochloride | Acute lymphoblastic leukemia; Chronic myelogenous leukemia |
| Pralatrexate | Peripheral T-cell lymphoma |
| Prednisone | Acute lymphoblastic leukemia; Chronic lymphocytic leukemia; Hodgkin lymphoma; Multiple myeloma; Non-Hodgkin lymphoma; Prostate cancer; Thymoma and thymic carcmoma |
| Procarbazine Hydrochloride | Hodgkin lymphoma |
| Provenge (Sipuleucel-T) | Prostate cancer |
| Purinethol (Mercaptopurine) | Acute lymphoblastic leukemia |
| Radium 223 Dichloride | Prostate cancer |
| Raloxifene Hydrochloride | Breast cancer |
| R-CHOP | Non-Hodgkin lymphoma |
| R-CVP | Non-Hodgkin lymphoma |
| Regorafenib | Colorectal cancer; Gastrointestinal stromal tumor |
| R-EPOCH | B-cell non-Hodgkin lymphoma |
| Revlimid (Lenalidomide) | Mantle cell lymphoma; Multiple myeloma; Anemia |
| Rheumatrex (Methotrexate) | Acute lymphoblastic leukemia; Breast cancer; Gestational trophoblastic disease; Head and neck cancer; Lung cancer; Non-Hodgkin lymphoma; Osteosarcoma |

TABLE 2-continued

| Cancer therapeutic agents | |
|---|---|
| Drug | Target(s) |
| Romidepsin | Cutaneous T-cell lymphoma |
| Rubidomycin (Daunorubicin Hydrochloride) | Acute lymphoblastic leukemia; Acute myeloid leukemia |
| Sipuleucel-T | Prostate cancer |
| Somatuline Depot (Lanreotide Acetate) | Gastroenteropancreatic neuroendocrine tumors |
| Sonidegib | Basal cell carcinoma |
| Sorafenib Tosylate | Hepatocellular carcinoma; Renal cell carcinoma; Thyroid cancer |
| Sprycel (Dasatinib) | Acute lymphoblastic leukemia; Chronic myelogenous leukemia |
| STANFORD V | Hodgkin lymphoma |
| Stivarga (Regorafenib) | Colorectal cancer; Gastrointestinal stromal tumor |
| Sunitnib Malate | Gastrointestinal stromal tumor; Pancreatic cancer; Renal cell carcinoma |
| Sutent (Sunitinib Malate) | Gastrointestinal stromal tumor; Pancreatic cancer; Renal cell carcinoma |
| Synovir (Thalidomide) | Multiple myeloma |
| Synribo (Omacetaxine Mepesuccinate) | Chronic myelogenous leukemia |
| TAC | Breast cancer |
| Tafinlar (Dabrafenib) | Melanoma |
| Tamoxifen Citrate | Breast cancer |
| Tarabine PFS (Cytarabine) | Acute lymphoblastic leukemia; Acute myeloid leukemia; Chronic myelogenous leukemia |
| Tarceva (Erlotinib Hydrochloride) | Non-small cell lung cancer; Pancreatic cancer |
| Targretin (Bexarotene) | Skin problems caused by cutaneous T-cell lymphoma |
| Tasigna (Niltinib) | Chronic myelogenous leukemia |
| Taxol (Paclitaxel) | AIDS-related Kaposi sarcoma; Breast cancer; Non-small cell lung cancer; Ovarian cancer |
| Taxotere (Docetaxel) | Breast cancer; Adenocarcinoma; Non-small cell lung cancer; Prostate cancer; Squamous cell carcinoma of the head and neck |
| Temodar (Temozolomide) | Anaplastic astrocytoma; Glioblastoma multiforme |
| Temozolomide | Anaplastic astrocytoma; Glioblastoma multiforme |
| Thiotepa | Bladder cancer; Breast cancer; Malignant pleural effusion, malignant pericardial effusion, and malignant peritoneal effusion; Ovarian cancer |
| Toposar (Etoposide) | Small cell lung cancer; Testicular cancer |
| Topotecan Hydrochloride | Cervical cancer; Ovarian cancer; Small cell lung cancer |
| Toremifene | Breast cancer |
| Torisel (Temsirolimus) | Renal cell carcinoma |
| TPF | Squamous cell carcinoma of the head and neck; Gastric (stomach) cancer |
| Treanda (Bendamustine Hydrochloride) | B-cell non-Hodgkin lymphoma; Chronic lymphocytic leukemia |
| Trisenox (Arsenic Trioxide) | Acute promyelocytic leukemia |
| Tykerb (Lapatinib Ditosylate) | Breast cancer |
| Vandetabib | Medullary thyroid cancer |
| VAMP | Hodgkin lymphoma |
| VeIP | Ovarian germ cell; Testicular cancer |
| Velban (Vinblastine Sulfate) | Breast cancer; Choriocarcinoma; Hodgkin lymphoma; Kaposi sarcoma; Mycosid fungoides; Non-Hodgkin lymphoma; Testicular cancer |
| Velcade (Bortezomib) | Multiple myeloma; Mantle cell lymphoma |
| Velsar (Vinblastine Sulfate) | Breast cancer; Choriocarcinoma; Hodgkin lymphoma; Kaposi sarcoma; Mycosis fungoides; Non-Hodgkin lymphoma; Testicular cancer |
| VePesid (Etoposide) | Small cell lung cancer; Testicular cancer |
| Viadur (Leuprolide Acetate) | Prostate cancer |
| Vidaza (Azacitidine) | Myelodysplastic syndromes |
| Vincasar PFS (Vincristine Sulfate) | Acute leukemia; Hodgkin lymphoma; Neuroblastoma; Non-Hodgkin lymphoma; Rhabdomyosarcoma; Wilms tumor |
| Vincristine Sulfate Liposome | Acute lymphoblastic leukemia |
| Vinorelbine Tartrate | Non-small cell lung cancer |
| VIP | Testicular cancer |
| Visbodegib | Basal cell carcinoma |
| Voraxaze (Glucarpidase) | Toxic blood levels of the anticancer drug methotrexate |
| Votrient (Pazopanib Hydrochloride) | Renal cell carcinoma; Soft tissue sarcoma |

TABLE 2-continued

| Cancer therapeutic agents | |
|---|---|
| Drug | Target(s) |
| Wellcovorin (Leucovorin Calcium) | Colorectal cancer; Anemia |
| Xalkori (Crizotinib) | Non-small cell lung cancer |
| Xeloda (Capecitabine) | Breast cancer; Colorectal cancer |
| XELIRI | Colorectal cancer; Esophageal cancer; Gastric (stomach) cancer |
| XELOX | Colorectal cancer |
| Xofigo (Radium 223 Dichloride) | Prostate cancer |
| Xtandi (Enzalutamide) | Prostate cancer |
| Zaltrap (Ziv-Aflibercept) | Colorectal cancer |
| Zelboraf (Vemurafenib) | Melanoma |
| Ziv-Aflibercept | Colorectal cancer |
| Zoladex (Goserelin Acetate) | Breast cancer; Prostate cancer |
| Zolinza (Vorinostat) | Cutaneous T-cell lymphoma |
| Zometa (Zoledronic Acid) | Multiple myeloma |
| Zydelig (Idelalisib) | Chronic lymphocytic leukemia; Non-Hodgkin lymphoma (Follicula B-cell non Hodgkin lymphoma and Small lymphocytic lymphoma) |
| Zykadia (Certinib) | Non-small cell lung cancer |
| Zytiga (Abiraterone Acetate) | Prostate cancer |

In some cases, a composition can be formulated to include nanoparticles containing carrier protein (e.g., nanoparticles with an albumin shell) that are complexed to a binding agent, therapeutic agents including at least doxorubicin and paclitaxel, at least doxorubicin and paclitaxel derivative, at least SN38 and paclitaxel, at least SN38 and paclitaxel derivative, or any combination of binding agents and therapeutic agents, e.g., those listed in Table 1 and Table 2, to form complexes for treating cancer. For example, carrier protein nanoparticles can be formulated to include bevacizumab to treat melanoma. Additional binding agents that target melanoma and therapeutic agents useful to treat melanoma can be included in the nanoparticles. In some cases, a composition can be formulated to include nanoparticles containing carrier protein (e.g., nanoparticles with an albumin shell) that are complexed (e.g., non-covalently bound) to a combination of different binding agents or therapeutic agents listed in Table 1 and Table 2 to form complexes capable of treating multiple different cancers. For example, carrier protein nanoparticles can be formulated to include trastuzumab, bevacizumab, and docetaxel as complexes for treating breast cancer and ovarian cancer.

In some cases, nanoparticles containing carrier protein (e.g., nanoparticles with an albumin shell) or a complex described herein (e.g., antibody-complexed albumin-bound therapeutic agent (e.g., doxorubicin or SN38)/paclitaxel or paclitaxel derivative nanoparticle complexes) can be formulated to include one or more anti-chronic inflammation treatment agents designed to reduce the global state of immune dysfunction and/or chronic inflammation present within a cancer patient. For example, steroidal anti-inflammatory agents (e.g., prednisone), non-steroidal anti-inflammatory agents (e.g., naproxen), lympho-depleting cytotoxic agents (e.g., cyclophosphamide), immune cell and/or cytokine targeting antibodies (e.g., infliximab), or a combination thereof can be incorporated into nanoparticles containing carrier protein or binding agent-complexed carrier protein-bound therapeutic agent (e.g., doxorubicin or SN38)/paclitaxel or paclitaxel derivative nanoparticle complexes. In some cases, anti-IL-4 agents (e.g., anti-IL-4 antibodies), anti-IL-13 agents (e.g., soluble IL-13 receptor), and combinations thereof can be incorporated into nanoparticles containing carrier protein or ABRAXANE®/binding agent complexes.

Any appropriate method can be used to assess whether or not the global state of immune dysfunction and/or chronic inflammation was reduced following an anti-chronic inflammation treatment. For example, cytokine profiles (e.g., IL-4, IL-13, IL-5, IL-10, IL-2, and interferon gamma) present in blood can be assessed before and after an anti-chronic inflammation treatment to determine whether or not the global state of immune dysfunction and/or chronic inflammation was reduced.

Nanoparticles and Nanoparticle Complexes

Any appropriate method can be used to obtain carrier protein-containing nanoparticles. For example, albumin may be combined with therapeutic agent (e.g., doxorubicin or SN38) and paclitaxel or paclitaxel derivative to form the nanoparticles.

The carrier protein-containing nanoparticles described herein may be formed by incubating the carrier protein (e.g., albumin) with paclitaxel or paclitaxel derivative (20-acetoxy-4-deacetyl-5-epi-20, O-secotaxol) and a therapeutic agent such as doxorubicin or SN38 under suitable conditions to form the nanoparticle. In some embodiments, the carrier protein is contacted with the doxorubicin and the paclitaxel at the same time. In embodiments, the carrier protein is contacted with the doxorubicin and the paclitaxel derivative (20-acetoxy-4-deacetyl-5-epi-20, O-secotaxol) at the same time. In embodiments, the carrier protein is contacted with SN38 and the paclitaxel at the same time. In embodiments, the carrier protein is contacted with SN38 and the paclitaxel derivative (20-acetoxy-4-deacetyl-5-epi-20, O-secotaxol) at the same time. In other embodiments, the carrier protein is contacted with paclitaxel first and then doxorubicin or vice versa. In embodiments, the carrier protein is contacted with the paclitaxel derivative (20-acetoxy-4-deacetyl-5-epi-20, O-secotaxol) first and then doxorubicin or vice versa. In other embodiments, the carrier protein is contacted with paclitaxel first and then SN38 or vice versa. In embodiments, the carrier protein is contacted with the paclitaxel derivative (20-acetoxy-4-deacetyl-5-epi-20, O-secotaxol) first and then SN38 or vice versa.

The ratio of doxorubicin to paclitaxel or SN38 to paclitaxel in the nanoparticle may be, for example, 5:1 to 1:20 therapeutic agent:paclitaxel by weight, e.g., 3:1 to 1:10, e.g., 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20, or any range therein. The ratio of doxorubicin to paclitaxel derivative or SN38 to paclitaxel derivative in the nanoparticle may be, for example, 5:1 to 1:20 therapeutic agent:paclitaxel derivative by weight, e.g., 3:1 to 1:10, e.g., 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20, or any range therein.

Any appropriate method can be used to obtain carrier protein-containing nanoparticles and a binding agent (a nanoparticle complex). For example, albumin may be combined with therapeutic agent (e.g., doxorubicin or SN38) and paclitaxel or paclitaxel derivative to form nanoparticles, which can then be combined with a binding agent to form a nanoparticle complex.

In one aspect, the nanoparticle complex of the present invention comprises at least 100 binding agents non-covalently bound to the surface of the nanoparticle. In one aspect, the nanoparticle complex comprises at least 200 binding agents non-covalently bound to the surface of the nanoparticle. In one aspect, the nanoparticle complex comprises at least 300 binding agents non-covalently bound to the surface of the nanoparticle. In one aspect, the nanoparticle complex comprises at least 400 binding agents non-covalently bound to the surface of the nanoparticle. In one aspect, the nanoparticle complex comprises at least 500 binding agents non-covalently bound to the surface of the nanoparticle. In one aspect, the nanoparticle complex comprises at least 600 binding agents non-covalently bound to the surface of the nanoparticle. In some embodiments, the binding agents may be Fe-fusion proteins, aptamers, and/or antibodies, e.g., anti-cancer antibodies.

In one aspect, the nanoparticle complex comprises between about 100 and about 1000 binding agents non-covalently bound to the surface of the nanoparticle. In one aspect, the nanoparticle complex comprises between about 200 and about 1000 binding agents non-covalently bound to the surface of the nanoparticle. In one aspect, the nanoparticle complex comprises between about 300 and about 1000 binding agents non-covalently bound to the surface of the nanoparticle complex. In one aspect, the nanoparticle complex comprises between about 400 and about 1000 binding agents non-covalently bound to the surface of the nanoparticle. In one aspect, the nanoparticle complex comprises between about 500 and about 1000 binding agents non-covalently bound to the surface of the nanoparticle. In one aspect, the nanoparticle complex comprises between about 600 and about 1000 binding agents non-covalently bound to the surface of the nanoparticle. In one aspect, the nanoparticle complex comprises between about 200 and about 800 binding agents non-covalently bound to the surface of the nanoparticle. In one aspect, the nanoparticle complex comprises between about 300 and about 800 binding agents non-covalently bound to the surface of the nanoparticle. In preferred embodiments, the nanoparticle complex comprises between about 400 and about 800 binding agents non-covalently bound to the surface of the nanoparticle. Contemplated values include any value or subrange within any of the recited ranges, including endpoints.

While not wishing to be bound to any theory, the inventors of the present application discovered that binding of paclitaxel or paclitaxel derivative to albumin specific to the albumin-paclitaxel or albumin-paclitaxel derivative nanoparticles opens an otherwise hidden binding site for hydrophobic binding of antibody on the nanoparticle, as disclosed in Butterfield et al. 2017 *Scientific Reports* 7(1):14476, incorporated herein by reference in its entirety. The binding site for antibodies is located relatively interiorly within the full HSA molecule and adjacent to a very hydrophobic drug binding site, paired with the lack of binding between the full antibodies and albumin from sources other than nab-paclitaxel (e.g., ABRAXANE®) particles, suggests that something in the process of albumin-bound paclitaxel or albumin-bound paclitaxel derivative nanoparticle formation permits antibody-albumin binding that otherwise would not happen. Whether this previously unknown unique binding site would remain open and stable during lyophilization was unknown and unpredictable.

The opening of the hidden binding site for antibody induced by paclitaxel or paclitaxel derivative is not inhibited by the addition of doxorubicin or SN38 to the nanoparticle. Indeed, the addition of a therapeutic agent (e.g., doxorubicin or SN38) enhances the characteristics of the nanoparticle complex compared to paclitaxel or paclitaxel derivative alone.

In some cases, complexes containing carrier protein-containing nanoparticles and binding agents (e.g., Fe-fusion proteins, aptamers, and/or antibodies) can be designed to have an average diameter that is greater than 1 μm. For example, appropriate concentrations of carrier protein-containing nanoparticles and binding agents can be used such that complexes having an average diameter that is greater than 1 μm are formed. In some cases, manipulations such as centrifugation can be used to form preparations of carrier protein-containing nanoparticle/binding agent complexes where the average diameter of those complexes is greater than 1 μm. In some cases, the preparations of carrier protein-containing nanoparticle/binding agent complexes provided herein can have an average diameter that is between 1 μm and 5 μm (e.g., between 1.1 μm and 5 μm, between 1.5 μm and 5 μm, between 2 μm and 5 μm, between 2.5 μm and 5 μm, between 3 μm and 5 μm, between 3.5 μm and 5 μm, between 4 μm and 5 μm, between 4.5 μm and 5 μm, between 1.1 μm and 4.5 μm, between 1.1 μm and 4 μm, between 1.1 μm and 3.5 μm, between 1.1 μm and 3 μm, between 1.1 μm and 2.5 μm, between 1.1 μm and 2 μm, or between 1.1 μm and 1.5 μm). Preparations of carrier protein-containing nanoparticle/binding agent complexes provided herein having an average diameter that is between 1 μm and 5 μm can be administered systemically (e.g., intravenously) to treat cancers located within a mammal's body. In some cases, the preparations of carrier protein-containing nanoparticle/binding agent complexes provided herein can have an average diameter that is between 5 μm and 50 μm (e.g., between 6 μm and 50 μm, between 7 μm and 50 μm, between 10 μm and 50 μm, between 15 μm and 50 μm, between 20 μm and 50 μm, between 25 μm and 50 μm, between 30 μm and 50 μm, between 35 μm and 50 μm, between 5 μm and 45 μm, between 5 μm and 40 μm, between 5 μm and 35 μm, between 5 μm and 30 μm, between 5 μm and 25 μm, between 5 μm and 20 μm, between 5 μm and 15 μm, or between 10 μm and 30 μm). Preparations of carrier protein-containing nanoparticle/binding agent complexes provided herein having an average diameter that is between 5 μm and 50 μm can be administered into a tumor (e.g., intratumorally) or in a region of a tumor located within a mammal's body.

Direct injection into a tumor includes injection into or proximal to a tumor site, perfusion into a tumor, and the like. When formulated for direct injection into a tumor, the nanoparticle complex may comprise any average particle size. Without being bound by any theory, it is believed that larger particles (e.g., greater than 500 nm, greater than 1 μm, and the like) are more likely to be immobilized within the tumor, thereby providing a beneficial effect. Larger particles can accumulate in the tumor or specific organs. See, e.g., 20-60 micron glass particle that is used to inject into the hepatic artery feeding a tumor of the liver, called "TheraSphere®" (in clinical use for liver cancer). Therefore, for intravenous administration, particles under 1 μm are typically used. Particles over 1 μm are, more typically, administered directly into a tumor ("direct injection") or into an artery feeding into the site of the tumor.

In some cases, a preparation of carrier protein-containing nanoparticle/binding agent complexes provided herein can have greater than 60 percent (e.g., greater than 65, 70, 75, 80, 90, 95, or 99 percent) of the complexes having a diameter that is between 1 μm and 5 μm (e.g., between 1.1 μm and 5 μm, between 1.5 μm and 5 μm, between 2 μm and 5 μm, between 2.5 μm and 5 μm, between 3 μm and 5 μm, between 3.5 μm and 5 μm, between 4 μm and 5 μm, between 4.5 μm and 5 μm, between 1.1 μm and 4.5 μm, between 1.1 μm and 4 μm, between 1.1 μm and 3.5 μm, between 1.1 μm and 3 μm, between 1.1 μm and 2.5 μm, between 1.1 μm and 2 μm, or between 1.1 μm and 1.5 μm). Preparation of carrier protein-containing nanoparticle/binding agent complexes provided herein having greater than 60 percent (e.g., greater than 65, 70, 75, 80, 90, 95, or 99 percent) of the complexes with a diameter that is between 1 μm and 5 μm can be administered systemically (e.g., intravenously) to treat cancers located within a mammal's body. In some cases, a preparation of carrier protein-containing nanoparticle/binding agent complexes provided herein can have greater than 60 percent (e.g., greater than 65, 70, 75, 80, 90, 95, or 99 percent) of the complexes having a diameter that is between 5 μm and 50 μm (e.g., between 6 μm and 50 μm, between 7 μm and 50 μm, between 10 μm and 50 μm, between 15 μm and 50 μm, between 20 μm and 50 μm, between 25 μm and 50 μm, between 30 μm and 50 μm, between 35 μm and 50 μm, between 5 μm and 45 μm, between 5 μm and 40 μm, between 5 μm and 35 μm, between 5 μm and 30 μm, between 5 μm and 25 μm, between 5 μm and 20 μm, between 5 μm and 15 μm, or between 10 μm and 30 μm). Preparation of carrier protein-containing nanoparticle/antibody complexes provided herein having greater than 60 percent (e.g., greater than 65, 70, 75, 80, 90, 95, or 99 percent) of the complexes with a diameter that is between 5 μm and 50 μm can be administered into a tumor (e.g., intratumorally) or in a region of a tumor located within a mammal's body. In some embodiments the nanoparticle complexes have the above average particle sizes either freshly made or after lyophilization and resuspension in an aqueous solution suitable for injection.

In one aspect, less than about 0.01% of the nanoparticle complexes within the composition have a particle size greater than 200 nm, greater than 300 nm, greater than 400 nm, greater than 500 nm, greater than 600 nm, greater than 700 nm, or greater than 800 nm. In one aspect, less than about 0.001% of the nanoparticle complexes within the composition have a particle size greater than 200 nm, greater than 300 nm, greater than 400 nm, greater than 500 nm, greater than 600 nm, greater than 700 nm, or greater than 800 nm. In a preferred embodiment, less than about 0.01% of the nanoparticle complexes within the composition have a particle size greater than 800 nm. In a more preferred embodiment, less than about 0.001% of the nanoparticle complexes within the composition have a particle size greater than 800 nm.

In some cases, complexes containing carrier protein-containing nanoparticles and binding agents (e.g., antibodies) can be designed to have an average diameter that is less than 1 μm. For example, appropriate concentrations of carrier protein-containing nanoparticles and binding agents can be used such that complexes having an average diameter that is less than 1 μm are formed. In some cases, the preparations of carrier protein-containing nanoparticle/binding agent complexes provided herein can have an average diameter that is between 0.05 μm and 1 μm (e.g., between 0.05 μm and 0.95 μm, between 0.05 μm and 0.9 μm, between 0.05 μm and 0.8 μm, between 0.05 μm and 0.7 μm, between 0.05 μm and 0.6 μm, between 0.05 μm and 0.5 μm, between 0.05 μm and 0.4 μm, between 0.05 μm and 0.3 μm, between 0.05 μm and 0.2 μm, between 0.2 μm and 1 μm, between 0.3 μm and 1 μm, between 0.4 μm and 1 μm, between 0.5 μm and 1 μm, between 0.2 μm and 0.6 μm, between 0.3 μm and 0.6 μm, between 0.2 μm and 0.5 μm, or between 0.3 μm and 0.5 μm). Preparations of carrier protein-containing nanoparticle/binding agent complexes provided herein having an average diameter that is between 0.05 μm and 0.9 μm can be administered systemically (e.g., intravenously) to treat cancers located within a mammal's body. In one aspect, the nanoparticle complex composition is formulated for intravenous injection. In order to avoid an ischemic event, the nanoparticle composition formulated for intravenous injection should comprise nanoparticles with an average particle size of less than about 1 μm.

In some cases, a preparation of carrier protein-containing nanoparticle/binding agent complexes provided herein can have greater than 60 percent (e.g., greater than 65, 70, 75, 80, 90, 95, or 99 percent) of the complexes having a diameter that is between 0.05 μm and 1 μm (e.g., between 0.05 μm and 0.95 μm, between 0.05 μm and 0.9 μm, between 0.05 μm and 0.8 μm, between 0.05 μm and 0.7 μm, between 0.05 μm and 0.6 μm, between 0.05 μm and 0.5 μm, between 0.05 μm and 0.4 μm, between 0.05 μm and 0.3 m, between 0.05 μm and 0.2 μm, between 0.2 μm and 1 μm, between 0.3 μm and 1 μm, between 0.4 μm and 1 μm, between 0.5 μm and 1 μm, between 0.2 μm and 0.6 μm, between 0.3 μm and 0.6 μm, between 0.2 μm and 0.5 μm, or between 0.3 μm and 0.5 μm). Preparation of carrier protein-containing nanoparticle/binding agent complexes provided herein having greater than 60 percent (e.g., greater than 65, 70, 75, 80, 90, 95, or 99 percent) of the complexes with a diameter that is between 0.05 μm and 1 μm can be administered systemically (e.g., intravenously) to treat cancers located within a mammal's body.

In some embodiments, the sizes and size ranges recited herein relate to particle sizes of the reconstituted lyophilized nanoparticle composition. That is, after the lyophilized nanoparticles are resuspended in an aqueous solution (e.g., water, other pharmaceutically acceptable excipient, buffer, etc.), the particle size or average particle size is within the range recited herein.

In one aspect, at least about 50%, 60%, 70%, 80%, 90%, 95%, 96%, 97%, 98%, 99%, 99.5%, or 99.9% of the nanoparticle complexes are present in the reconstituted composition as single nanoparticles. That is, fewer than about 50%, 40%, 30%, etc. of the nanoparticle complexes are dimerized or multimerized (oligomerized).

In some embodiments, the size of the nanoparticle complex can be controlled by the adjusting the amount (e.g., ratio) of carrier protein to binding agent. The size of the nanoparticle complex, and the size distribution, is also important. The nanoparticle complexes described herein may behave differently according to their size. At large sizes, an agglomeration may block blood vessels. Therefore, agglomeration of nanoparticle complexes can affect the performance and safety of the composition. On the other hand, larger particle complexes (e.g., multimers) may be more therapeutic under certain conditions (e.g., when not administered intravenously).

In general, carrier protein-containing nanoparticles can be contacted with a binding agent such as polypeptide antibody prior to administration to a human to form a carrier protein-containing nanoparticle/binding agent complex (e.g., an albumin/doxorubicin/paclitaxel particle/anti-VEGF polypeptide antibody complex, albumin/SN38/paclitaxel particle/anti-VEGF polypeptide antibody complex, albumin/doxorubicin/paclitaxel derivative particle/anti-VEGF polypeptide antibody complex, albumin/SN38/paclitaxel derivative particle/anti-VEGF polypeptide antibody complex, an albumin/doxorubicin/paclitaxel particle/anti-CD20 polypeptide antibody complex, albumin/SN38/paclitaxel particle/anti-CD20 polypeptide antibody complex, albumin/doxorubicin/paclitaxel derivative particle/anti-CD20 polypeptide antibody complex, albumin/SN38/paclitaxel derivative particle/anti-CD20 polypeptide antibody complex, an albumin/doxorubicin/paclitaxel particle/anti-PDL1 polypeptide antibody complex, albumin/SN38/paclitaxel particle/anti-PDL1 polypeptide antibody complex, albumin/doxorubicin/paclitaxel derivative particle/anti-PDL1 polypeptide antibody complex, albumin/SN38/paclitaxel derivative particle/anti-PDL1 polypeptide antibody complex, etc.). Any appropriate carrier protein-containing nanoparticle preparation and any appropriate binding agent can be used as described herein. For example, albumin/doxorubicin/paclitaxel particle nanoparticles, albumin/doxorubicin/paclitaxel derivative (20-acetoxy-4-deacetyl-5-epi-20, O-secotaxol) particle nanoparticles, albumin/SN38/paclitaxel particle nanoparticles, or albumin/SN38/paclitaxel derivative (20-acetoxy-4-deacetyl-5-epi-20, O-secotaxol) particle nanoparticles can be used as described herein. Examples of binding agents that can be used to form carrier protein-containing nanoparticle/binding agent complexes as described herein include, without limitation, those listed in Table 1. For example, an appropriate dose of albumin/doxorubicin or SN38/paclitaxel or paclitaxel derivative (20-acetoxy-4-deacetyl-5-epi-20, O-secotaxol) particles and an appropriate dose of a binding agent can be mixed together in the same container. This mixture can be incubated at an appropriate temperature of about 5° C. to about 60° C., or any range, subrange, or value within that range including endpoints. In embodiments, the mixture can be incubated at room temperature, e.g., between about 15° C. and about 30° C., between about 15° C. and about 25° C., between about 20° C. and about 30° C., or between about 20° C. and about 25° C. for a period of time (e.g., about 30 minutes, or between about 5 minutes and about 60 minutes, between about 5 minutes and about 45 minutes, between about 15 minutes and about 60 minutes, between about 15 minutes and about 45 minutes, between about 20 minutes and about 40 minutes, or between about 25 minutes and about 35 minutes) before being administered to a cancer patient.

In some cases, carrier protein-containing nanoparticles can be contacted with a binding agent to form carrier protein-containing nanoparticle/binding agent complexes that are stored prior to being administered to a cancer patient. For example, a composition containing carrier protein-containing nanoparticle/binding agent complexes can be formed as described herein and stored for a period of time (e.g., days or weeks) prior to being administered to a cancer patient.

In one embodiment, the binding agents of the nanoparticle complexes are integrated onto and/or into the nanoparticle complexes, e.g. on the surface of a carrier protein-bound therapeutic agent (e.g., doxorubicin or SN38)/paclitaxel core. In one embodiment, the binding agents of the nanoparticle complexes are arranged on a surface of a carrier protein (e.g., albumin)-bound therapeutic agent (e.g., doxorubicin or SN38)/paclitaxel core. In one embodiment, the binding agents of the nanoparticle complexes are associated with a carrier protein-bound therapeutic agent (e.g., doxorubicin or SN38)/paclitaxel core. In embodiments, the binding agents of the nanoparticle complexes are integrated onto and/or into the nanoparticle complexes, e.g. on the surface of a carrier protein-bound therapeutic agent (e.g., doxorubicin or SN38)/paclitaxel derivative core. In embodiments, the binding agents of the nanoparticle complexes are arranged on a surface of a carrier protein (e.g., albumin)-bound therapeutic agent (e.g., doxorubicin or SN38)/paclitaxel derivative core. In embodiments, the binding agents of the nanoparticle complexes are associated with a carrier protein-bound therapeutic agent (e.g., doxorubicin or SN38)/paclitaxel derivative core. In one embodiment, the binding agents of the nanoparticle complexes are non-covalently associated with (bound to) a carrier protein, e.g., albumin, in the nanoparticle complex. In one embodiment, the carrier protein (e.g., albumin) and therapeutic agents, e.g., doxorubicin, SN38 and paclitaxel (or paclitaxel derivative), are associated (bound to each other) via non-covalent bonds.

In one aspect, the nanoparticle complexes of the nanoparticle composition are formed by contacting the carrier protein or carrier protein-therapeutic agent particle with the binding agent at a ratio of about 50:1 to about 10:30 (by concentration) of carrier protein particle or carrier protein-therapeutic agent particle to binding agent. In one embodiment, the ratio is about 50:2 to about 10:25. In one embodiment, the ratio is about 50:2 to about 1:1. In one embodiment, the ratio is about 50:2 to about 10:6. In one embodiment, the ratio is about 50:4. In one embodiment, the ratio is about 50:2. Contemplated ratios include any value, subrange, or range within any of the recited ranges, including endpoints.

In one embodiment, the amount of solution or other liquid medium employed to form the nanoparticle complexes is particularly important. No nanoparticle complexes are formed in an overly dilute solution of the carrier protein (or carrier protein-therapeutic agent) and the binding agents. An overly concentrated solution will result in unstructured aggregates. In some embodiments, the amount of solution (e.g., sterile water, saline, phosphate buffered saline) employed is between about 0.5 mL of solution to about 20 mL of solution. In some embodiments, the concentration of carrier protein (or carrier protein-therapeutic agent) nanoparticles is between about 1 mg/mL and about 100 mg/mL. In some embodiments, the concentration of antibody is between about 0.04 mg/mL and about 4 mg/mL. For example, in some embodiments, the ratio of carrier protein: binding agent solution is approximately 25 mg of carrier protein (e.g., albumin) to 1 mg of binding agent (e.g., antibody) in 1 mL of solution (e.g., saline). The therapeutic agents (e.g., doxorubicin, SN38 and paclitaxel) can also be added to the carrier protein. When using a typical i.v. bag, for example, with the solution of approximately 1 liter one would need to use 1000× the amount of carrier protein/carrier protein-therapeutic agent and binding agent compared to that used in 1 mL. Thus, one cannot form the present nanoparticles in a standard i.v. bag. Furthermore, when the components are added to a standard i.v. bag in the therapeutic amounts of the present invention, the components do not self-assemble to form nanoparticle complexes.

In one embodiment, the carrier protein or carrier protein-therapeutic agent(s) particle is contacted with the binding agent in a solution having a pH between about 4 and about 8. In one embodiment, the carrier protein or carrier protein-therapeutic agent(s) particle is contacted with the binding agent in a solution having a pH of about 4. In one embodiment, the carrier protein or carrier protein-therapeutic agent (s) particle is contacted with the binding agent in a solution having a pH of about 5. In one embodiment, the carrier protein or carrier protein-therapeutic agent(s) particle is contacted with the binding agent in a solution having a pH of about 6. In one embodiment, the carrier protein or carrier protein-therapeutic agent(s) particle is contacted with the binding agent in a solution having a pH of about 7. In one embodiment, the carrier protein or carrier protein-therapeutic agent(s) particle is contacted with the binding agent in a solution having a pH of about 8. In a preferred embodiment, the carrier protein or carrier protein-therapeutic agent(s) particle is contacted with the binding agent in a solution having a pH between about 5 and about 7.

Without being bound by any theory, it is believed that the stability of the nanoparticle complexes within the nanoparticle composition is, at least in part, dependent upon the temperature and/or pH at which the nanoparticle complexes are formed, as well as the concentration of the components (i.e., carrier protein, binding agent, and optionally therapeutic agent) in the solution. In one embodiment, the $K_d$ of the nanoparticle complexes is between about $1\times10^{-1}$ M and about $2\times10^{-5}$ M. In one embodiment, the $K_d$ of the nanoparticle complexes is between about $1\times10^{-11}$ M and about $2\times10^{-8}$ M. In one embodiment, the $K_d$ of the nanoparticle complexes is between about $1\times10^{-11}$ M and about $7\times10^{-9}$ M. In a preferred embodiment, the $K_d$ of the nanoparticle complexes is between about $1\times10^{-11}$ M and about $3\times10^{-8}$ M. Contemplated values include any value, subrange, or range within any of the recited ranges, including endpoints.

Lyophilization

The lyophilized compositions described herein, are prepared by standard lyophilization techniques with or without the presence of stabilizers, buffers, etc. Surprisingly, these conditions do not alter the relatively fragile structure of the nanoparticle complexes. Moreover, at best, these nanoparticle complexes retain their size distribution or even increase their size distribution upon lyophilization and, more importantly, can be reconstituted for in vivo administration (e.g., intravenous delivery) in substantially the same form and ratios as if freshly made.

The current invention is further predicated, in part, on the surprising discovery that optionally lyophilized nanoparticles comprising a carrier protein, a binding agent, e.g., an antibody, an aptamer, or a fusion protein having a hydrophobic domain and a binding domain, e.g., an Fc domain fused to an aptamer or the ligand of a cellular receptor, and a therapeutic agent provide targeted therapy to a tumor while minimizing toxicity to the patient. The nanoparticles as described herein are thus a significant improvement versus conventional ADCs.

Lyophilization, or freeze drying, removes water from a composition. In the process, the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al., Pharm. Res. 8(3):285-291 (1991).

While proteins may be lyophilized, the process of lyophilization and reconstitution may affect the properties of the protein. Because proteins are larger and more complex than traditional organic and inorganic drugs (i.e., possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e., any process which involves modification of the protein by bond formation or cleavage resulting in a new chemical entity) or physical instability (i.e., changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland, et al., Critical Reviews in Therapeutic Drug Carrier Systems 10(4): 307-377 (1993).

The composition provided herein comprises nanoparticles which contain (a) carrier protein (b) binding agent and (c) therapeutic agents. The binding agent is non-covalently bound to the carrier protein, possibly through hydrophobic interactions which by their nature, are weak. The lyophilization and reconstitution of such a composition must, therefore, not only preserve the activity of the individual components, but also their relative relationship in the nanoparticle. Yet the activity of the individual components, as well as their relative relationship in the nanoparticle, is preserved despite lyophilization and reconstitution of the composition. It is still further contemplated that binding to the carrier protein, e.g., complexation of the binding agent to the carrier protein, occurs through some or all of the hydrophobic portion of the binding agent, e.g., the Fc component of an antibody, which results in all or part of the hydrophobic portion being integrated into the carrier protein core, while the target binding portions (regions) (e.g., an Fa and Fb portion of the antibody) remain outside of the carrier protein core, thereby retaining their target specific binding capabilities. In some embodiments, the binding agent is a non-therapeutic and non-endogenous human antibody, a fusion protein, e.g., fusion of an antibody Fc domain to a peptide that binds a target antigen, or an aptamer.

Further challenges are imposed because the nanoparticle complexes are used in therapy. For example, rearrangement of the hydrophobic components in the nanoparticle complex may be mitigated through covalent bonds between the components. However, such covalent bonds pose challenges for the therapeutic use of nanoparticle complexes in cancer treatment. The binding agent, carrier protein, and additional therapeutic agent typically act at different locations in a tumor and through different mechanisms. Non-covalent bonds permit the components of the nanoparticle complex to dissociate at the tumor. Thus, while a covalent bond may be advantageous for lyophilization, it may be disadvantageous for therapeutic use.

The size of the nanoparticle complexes, and the distribution of the size, is also important. The nanoparticle complexes described herein may behave differently according to their size. At large sizes, the nanoparticle complexes or the agglomeration of these particles may block blood vessels either of which can affect the performance and safety of the composition. Finally, cryoprotectants and agents that assist in the lyophilization process must be safe and tolerated for therapeutic use.

For conventional ADCs to be effective, it is critical that the linker be stable enough not to dissociate in the systemic circulation but allow for sufficient drug release at the tumor site. Alley, S. C., et al. (2008) *Bioconjug Chem* 19:759-765. This has proven to be a major hurdle in developing effective drug conjugates (Julien, D. C., et al. (2011) MAbs 3:467-478; Alley, S.C., et al. (2008) *Bioconjug Chem* 19:759-765); therefore, an attractive feature of the nanoparticle complex is that a biochemical linker is not required.

Another shortcoming of current ADCs is that higher drug penetration into the tumor has not been substantively proven in human tumors. Early testing of ADCs in mouse models suggested that tumor targeting with antibodies would result in a higher concentration of the active agent in the tumor (Deguchi, T. et al. (1986) *Cancer Res* 46: 3751-3755); however, this has not correlated in the treatment of human disease, likely because human tumors are much more heterogeneous in permeability than mouse tumors. Jain, R. K. et al. (2010) *Nat Rev Clin Oncol* 7:653-664. Also, the size of the nanoparticle complex is critical for extravasation from the vasculature into the tumor. In a mouse study using a human colon adenocarcinoma xenotransplant model, the vascular pores were permeable to liposomes up to 400 nm. Yuan, F., et al. (1995) *Cancer Res* 55: 3752-3756. Another study of tumor pore size and permeability demonstrated that both characteristics were dependent on tumor location and growth status, with regressing tumors and cranial tumors permeable to particles less than 200 nm. Hobbs, S. K., et al. (1998) *Proc Natl Acad Sci USA* 95:4607-4612. The nanoparticle complex described herein overcomes this issue by the fact that the large complex, which is less than 200 nm intact, is partially dissociated in systemic circulation into smaller functional units that are easily able to permeate tumor tissue. Furthermore, once the complex arrives to the tumor site, the smaller toxic payload can be released and only the toxic portion needs to be taken up by tumor cells, not the entire conjugate.

The advent of antibody- (i.e., AVASTIN®) coated albumin nanoparticles containing a therapeutic agent (i.e., paclitaxel) has led to a new paradigm of directional delivery of two or more therapeutic agents to a predetermined site in vivo. See PCT Patent Publication Nos. WO 2012/154861, WO 2014/055415, WO 2015/191969, WO 2015/195476, WO 2016/057554, WO 2017/031368, WO 2017/176265, WO 2018/048816, and WO 2018/048958.

While protein compositions comprising a single source protein are commonly stored in lyophilized form where they exhibit significant shelf-life, such lyophilized compositions do not contain a self-assembled nanoparticle of two different proteins integrated together by hydrophobic-hydrophobic interactions. Moreover, the nanoparticle configuration wherein a majority of the antibody binding portions are exposed on the surface of the nanoparticles lends itself to being susceptible to dislodgement or reconfiguration by conditions which otherwise would be considered benign. For example, during lyophilization, ionic charges on the proteins are dehydrated thereby exposing the underlying charges. Exposed charges allow for charge-charge interactions between the two proteins which can alter the binding affinity of each protein to the other. In addition, the concentration of the nanoparticles increases significantly as the solvent (e.g., water) is removed. Such increased concentrations of nanoparticles could lead to irreversible oligomerization. Oligomerization is a known property of proteins that reduces the biological properties of the oligomer as compared to the monomeric form and increases the size of the particle sometimes beyond 1 micron.

On the other hand, a stable form of a nanoparticle composition is required for clinical and/or commercial use where a shelf-life of at least 3 months is required and shelf-lives of greater than 6 months or 9 months are preferred. Such a stable composition must be readily available for intravenous injection, must retain its self-assembled form upon intravenous injection so as to direct the nanoparticle to the predetermined site in vivo, must have a maximum size of less than 1 micron so as to avoid any ischemic event when delivered into the blood stream, and finally must be compatible with the aqueous composition used for injection.

When the therapeutic efficacy of nanoparticle complexes similar to those of the present invention was compared side-by-side, the results surprisingly demonstrated that lyophilized and reconstituted complex retains activity equivalent to or greater than fresh complex. Additionally, the diameter of the complexes is on average larger post-lyophilization than pre-lyophilization. This increase in diameter may be due to the antibodies being more densely packed onto the nanoparticle due to decreased water following the lyophilization process. As there are increasing improvements in tumor size reduction and survival of bevacizumab nanoparticle complexes between the sizes of 160 nm up to 1130 nm (Nevala et al. 2016 Cancer Res (76)13:3954-3964), lyophilization unexpectedly improves the product by producing a complex with increased average diameter post reconstitution.

Pharmaceutical Compositions and Methods of Using Nanoparticle Complexes

In general, the complexes provided herein can be formulated for administration to a patient by any of the accepted modes of administration. Various formulations and drug delivery systems are available in the art. See, e.g., Gennaro, A. R., ed. (2012) *Remington's Pharmaceutical Sciences*, $22^{nd}$ ed., Mack Publishing Co.

In general, complexes provided herein will be administered as pharmaceutical compositions by any one of the following routes: oral, systemic (e.g., transdermal, intranasal or by suppository), or parenteral (e.g., intramuscular, intravenous or subcutaneous) administration.

In one aspect, the pharmaceutical composition of nanoparticle complexes described herein is formulated for direct injection into a tumor. Direct injection includes injection into or proximal to a tumor site, perfusion into a tumor, and the like. Because the pharmaceutical composition of nanoparticle complexes is not administered systemically, a pharmaceutical composition of nanoparticle complexes is formulated for direct injection into a tumor may comprise any average particle size. Without being bound by any theory, it is believed that larger particles (e.g., greater than 600 nm, greater than 1 μm, and the like) are more likely to be immobilized within the tumor, thereby providing what is believed to be a better beneficial effect.

In an aspect, provided herein is a pharmaceutical composition of the nanoparticle complexes described herein. The pharmaceutical compositions are comprised of, in general, nanoparticle complexes described herein in combination with at least one pharmaceutically acceptable excipient. Acceptable excipients are non-toxic, aid administration, and do not adversely affect the therapeutic benefit of the claimed complexes. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, $22^{nd}$ ed., 2012).

The present formulations may, if desired, be presented in a pack or dispenser device containing a unit-dose of the active ingredient. Such a pack or device may, for example, comprise metal or plastic foil, such as a blister pack, or glass, and rubber stoppers such as in vials. The pack or dispenser device may be accompanied by instructions for administration. Pharmaceutical compositions described herein, comprising a unit-dose formulation formulated in a compatible pharmaceutical carrier may also be prepared, placed in an appropriate container, and labeled for treatment of an indicated condition.

Any appropriate method can be used to administer a carrier protein-containing nanoparticle/antibody complex provided herein (e.g., an antibody-complexed albumin-bound therapeutic agent/paclitaxel nanoparticle complex or an antibody-complexed albumin-bound therapeutic agent/paclitaxel derivative nanoparticle complex) to a mammal. For example, a pharmaceutical composition containing carrier protein-containing nanoparticle/binding agent complexes can be administered via injection (e.g., subcutaneous injection, intramuscular injection, intravenous injection, or intrathecal injection).

The nanoparticle complexes and pharmaceutical compositions of nanoparticle complexes as described herein are useful in treating cancer cells and/or tumors in a mammal. In an embodiment, the mammal is a human (i.e., a human patient). In embodiments, a lyophilized nanoparticle complex or pharmaceutical composition of a nanoparticle complex is reconstituted (suspended in an aqueous excipient) prior to administration.

In one aspect is provided a method for treating a cancer cell, the method comprising contacting the cell with an effective amount of the nanoparticle complex or the pharmaceutical composition of the nanoparticle complex as described herein to treat the cancer cell. Treatment of a cancer cell includes, without limitation, reduction in proliferation, killing the cell, preventing metastasis of the cell, and the like.

In one aspect is provided a method for treating a tumor in a patient in need thereof, the method comprising administering to the patient a therapeutically effective amount of a nanoparticle complex or a pharmaceutical composition of the nanoparticle complex as described herein to treat the tumor. In one embodiment, the size of the tumor is reduced. In one embodiment, the tumor size does not increase (i.e., progress) for at least a period of time during and/or after treatment.

In one embodiment, the nanoparticle complex or the pharmaceutical composition of the nanoparticle complex is administered intravenously. In one embodiment, the nanoparticle complex or the pharmaceutical composition of the nanoparticle complex is administered directly to the tumor. In one embodiment, the nanoparticle complex or the pharmaceutical composition of the nanoparticle complex is administered by direct injection or perfusion into the tumor.

In one embodiment, the method comprises: a) administering the nanoparticle complex or the pharmaceutical composition of the nanoparticle complex once a week for three weeks; b) ceasing administration of the nanoparticle complex or the pharmaceutical composition of the nanoparticle complex for one week; and c) optionally repeating steps a) and b) as necessary to treat the tumor.

In one embodiment, the therapeutically effective amount of the nanoparticle complexes described herein comprises about 50 $mg/m^2$ to about 200 $mg/m^2$ carrier protein or carrier protein and therapeutic agent. In some embodiments, the therapeutically effective amount comprises about 75 $mg/m^2$ to about 175 $mg/m^2$ carrier protein or carrier protein and therapeutic agent. Contemplated values include any value, subrange, or range within any of the recited ranges, including endpoints.

In one embodiment, the therapeutically effective amount comprises about 2 $mg/m^2$ to about 9 $mg/m^2$ binding agent, e.g., antibody, aptamer, or Fc fusion. In some embodiments, the therapeutically effective amount comprises 3 $mg/m^2$ to about 7 $mg/m^2$ binding agent. Contemplated values include any value, subrange, or range within any of the recited ranges, including endpoints.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; renal cancer including adenocarcinoma and Wilms tumor; and those cancers listed in Table 1 and Table 2.

In general, the compounds described herein will be administered in a therapeutically effective amount by any of the accepted modes of administration for agents that serve similar utilities. The actual amount of the compound of this invention, i.e., the nanoparticle complexes, will depend upon numerous factors such as the severity of the disease to be treated, the age and relative health of the subject, the potency of the compound used, the route and form of administration, and other factors well known to the skilled artisan.

An effective amount of such compounds can readily be determined by routine experimentation, as can the most effective and convenient route of administration, and the most appropriate formulation. Various formulations and drug delivery systems are available in the art. See, e.g., Gennaro, A. R., ed. (2012) *Remington's Pharmaceutical Sciences,* 22nded., Mack Publishing Co.

An effective amount or a therapeutically effective amount or dose of a compound described herein, refers to that amount of the compound that results in amelioration of symptoms or a prolongation of survival in a subject. Toxicity and therapeutic efficacy of such compounds can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. compounds that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the compound may not be related to plasma concentration.

Before administering a composition containing a carrier protein-containing nanoparticle/binding agent complex provided herein to a mammal, the mammal can be assessed to determine whether or not the mammal has cancer. Any appropriate method can be used to determine whether or not a mammal has cancer. For example, a mammal (e.g., human) can be identified as having cancer (e.g., skin cancer, e.g., lymphoma) using standard diagnostic techniques. In some cases, a tissue biopsy (e.g., a skin biopsy, e.g., a lymph node biopsy) can be collected and analyzed to determine whether or not a mammal has cancer.

After identifying a mammal as having cancer, the mammal can be administered a composition containing carrier protein-containing nanoparticle/binding agent complexes as provided herein. For example, a composition comprising carrier protein-containing nanoparticle/binding agent complexes (e.g., antibody-complexed albumin-bound paclitaxelnanoparticle complexes) can be administered prior to or in lieu of surgical resection of a tumor. In some cases, a composition containing carrier protein-containing nanoparticle/binding agent complexes as provided herein (e.g., antibody-complexed albumin-bound doxorubicin/paclitaxel nanoparticle complexes) can be administered following resection of a tumor.

In embodiments, a composition containing carrier protein-containing nanoparticle/binding agent complexes as provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be administered to a mammal in any appropriate amount, at any appropriate frequency, and for any appropriate duration effective to achieve a desired outcome (e.g., to increase progression-free survival). In some cases, a composition containing carrier protein-containing nanoparticle/binding agent complexes as provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be administered to a mammal having cancer to reduce the progression rate of the cancer by 5, 10, 25, 50, 75, 100, or more percent. For example, the progression rate can be reduced such that no additional cancer progression is detected. Any appropriate method can be used to determine whether or not the progression rate of cancer is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate was reduced.

In some cases, a composition containing carrier protein-containing nanoparticle/binding agent complexes as provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be administered to a mammal having cancer under conditions where progression-free survival is increased (e.g., by 5, 10, 25, 50, 75, 100, or more percent) as compared to the median progression-free survival of corresponding mammals having untreated cancer or the median progression-free survival of corresponding mammals having cancer treated with a nanoparticle and a binding agent without forming carrier protein-containing nanoparticle/binding agent complexes (e.g., without forming antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes). In some cases, a composition containing carrier protein-containing nanoparticle/binding agent complexes as provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be administered to a mammal having cancer to increase progression-free survival by 5, 10, 25, 50, 75, 100, or more percent as compared to the median progression-free survival of corresponding mammals having cancer and having received a nanoparticle or a binding agent alone. Progression-free survival can be measured over any length of time (e.g., one month, two months, three months, four months, five months, six months, or longer).

In some cases, a composition containing carrier protein-containing nanoparticle/binding agent complexes as provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be administered to a mammal having cancer under conditions where the 8-week progression-free survival rate for a population of mammals is 65% or greater (e.g., 66%, 67%, 68%, 69%, 70%, 71%, 72%, 73%, 74%, 75%, 76%, 77%, 78%, 79%, 80% or greater) than that observed in a population of comparable mammals not receiving a composition containing carrier protein-containing nanoparticle/binding agent complexes provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes). In some cases, a composition containing carrier protein-containing nanoparticle/binding agent complexes as provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be administered to a mammal having cancer under conditions where the median time to progression for a population of mammals is at least 150 days (e.g., at least 155, 160, 163, 165, or 170 days).

An effective amount of a composition containing carrier protein-containing nanoparticle/binding agent complexes as provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be any amount that reduces the progression rate of cancer, increases the progression-free survival rate, or increases the median time to progression without producing significant toxicity to the mammal. Typically, an effective amount of albumin/therapeutic agent/paclitaxel can be from about 50 mg/m$^2$ to about 150 mg/m$^2$ (e.g., about 80 mg/m$^2$), and an effective amount of a binding agent, e.g., an antibody, e.g., an anti-VEGF polypeptide antibody such as bevacizumab or biosimilar versions thereof, e.g., an anti-CD20 polypeptide antibody such as rituximab or biosimilar versions thereof, can be from about 1 mg/kg to about 20 mg/kg (e.g., about 3 mg/kg). If a particular mammal fails to respond to a particular amount, then the amount of albumin/therapeutic agent/paclitaxel or binding agent can be increased by, for example, two-fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that reduces the progression rate of cancer, increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing carrier protein-containing nanoparticle/binding agent complexes provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can include rest periods. For example, a composition described herein can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the skin cancer may require an increase or decrease in administration frequency.

An effective duration for administering a composition provided herein can be any duration that reduces the progression rate of cancer, increases the progression-free survival rate, or increases the median time to progression without producing significant toxicity to the mammal. Thus, the effective duration can vary from several days to several weeks, months, or years. In general, the effective duration for the treatment of skin cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer.

A composition containing carrier protein-containing nanoparticle/binding agent complexes provided herein (e.g., antibody-complexed albumin-bound doxorubicin/paclitaxel nanoparticle complexes, antibody-complexed albumin-bound SN38/paclitaxel nanoparticle complexes, antibody-complexed albumin-bound doxorubicin/paclitaxel derivative nanoparticle complexes, or antibody-complexed albumin-bound SN38/paclitaxel derivative nanoparticle complexes) can be in any appropriate form. For example, a composition provided herein can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, mannitol, or combinations thereof.

After administering a composition provided herein to a mammal, the mammal can be monitored to determine whether or not the cancer was treated. As described herein, any method can be used to assess progression and survival rates.

In one aspect is provided a method for treating a patient suffering from a cancer which expresses an antigen (e.g., an antigen listed in Table 1) wherein said patient is treated with a sub-therapeutic amount of a binding agent specific against the antigen (e.g., an antibody listed in Table 1) and carrier protein-bound chemotherapeutic/binding agent nanoparticle complexes containing a therapeutically effective amount of the chemotherapeutic such that the administration of said sub-therapeutic amount of the anti-antigen binding agent (e.g., antibody) enhances the efficacy of said nanoparticle complexes.

For the sake of clarification, "co-treatment" refers to treatment of the cancer expressing the antigen (e.g., VEGF; a soluble cytokine) with an anti-antigen (e.g., anti-VEGF) binding agent prior, concurrent or immediately after administration of the carrier protein-bound chemotherapeutic/anti-antigen binding agent complex provided that the anti-antigen antibody is capable of preferentially binding soluble antigen.

In one embodiment, the anti-antigen binding agent is administered in a sub-therapeutic dose prior to the nanoparticle complex. In this embodiment, the administration of the anti-antigen binding agent occurs about 0.5 to 48 hours prior to administration of the nanoparticle complexes.

In another embodiment, the anti-antigen binding agent composition is administered between 0.5 hours prior to and up to 0.5 hours after administration of the nanoparticle complexes. In this embodiment, it is contemplated that such administration will nevertheless result in binding of some of the circulating antigen (e.g., VEGF) by the binding agent (e.g., antibody) composition.

In yet another embodiment, the antibody composition can be administered up to 2 hours post administration of the nanoparticle complexes.

In one aspect, provided herein are methods for enhancing the efficacy of carrier protein-bound chemotherapeutic/anti-antigen binding agent nanoparticle complexes by administering the carrier protein-bound chemotherapeutic/anti-antigen binding agent nanoparticle complexes about 0.5 to 48 hours after pretreatment of a patient with a sub-therapeutic amount of anti-antigen binding agent. In one embodiment, such nanoparticle complexes are administered about 24 hours after the sub-therapeutic amount of anti-antigen binding agent.

In another aspect, provided herein are methods for enhancing the therapeutic outcome in a patient suffering from a cancer expressing soluble antigen (e.g., VEGF) which patient is selected to be treated with nanoparticles comprising carrier protein-bound doxorubicin/paclitaxel or carrier protein-bound SN38/paclitaxel and anti-antigen binding agents wherein said binding agents of the nanoparticles are integrated onto and/or into said nanoparticles which method comprises treating said patient with a sub-therapeutic amount of said anti-antigen binding agent prior to any subsequent treatment with the nanoparticles.

In another aspect, provided herein are methods for enhancing the therapeutic outcome in a patient suffering from a cancer overexpressing soluble antigen (e.g., VEGF), said method comprising treating the patient with a sub-therapeutic amount of said anti-antigen binding agent and co-treating said patients with an effective amount of nanoparticles comprising carrier protein-bound doxorubicin/paclitaxel or carrier protein-bound SN38/paclitaxel and anti-antigen binding agents wherein said binding agents of the nanoparticles are integrated onto and/or into said nanoparticles.

In another aspect, provided herein is a method for enhancing the therapeutic outcome in a patient suffering from a cancer expressing soluble antigen (e.g., VEGF) which patient is to be treated with nanoparticles comprising carrier protein-bound doxorubicin/paclitaxel or carrier protein-bound SN38/paclitaxel and anti-antigen binding agents wherein said binding agents of the nanoparticles are integrated onto and/or into said nanoparticles which method comprises treating said patient with a sub-therapeutic amount of said anti-antigen binding agent within +/−0.5 hours of administration of said nanoparticles.

In another aspect provided herein is a method for enhancing the therapeutic outcome in a patient suffering from a cancer overexpressing soluble antigen (e.g., VEGF) which patient has been treated with a sub-therapeutic amount of said anti-antigen binding agent said method comprising treating said patients with an effective amount of nanoparticles comprising carrier protein-bound doxorubicin/paclitaxel or carrier protein-bound SN38/paclitaxel and anti-antigen binding agents wherein said binding agents of the nanoparticles are integrated onto and/or into said nanoparticle antibody within +/−0.5 hours of administration of said binding agents.

The patient may be co-treated with a sub-therapeutic amount of an anti-antigen binding agent and carrier protein-bound chemotherapeutic/anti-antigen binding agent complex.

In some embodiments the anti-antigen binding agent is administered prior to the carrier protein-bound chemotherapeutic/anti-antigen binding agent complex, for example, the binding agent can be administered minutes, hours or days prior to administration of the carrier protein-bound chemotherapeutic/binding agent complex. In some embodiments, the binding agent is administered between about 5 to about 59 minutes, about 10 to about 50 minutes, about 15 to about 45 minutes, about 20 to about 40 minutes, about 25 to about 35 minutes prior to administration of the carrier protein-bound chemotherapeutic/binding agent complex. In other embodiments, the binding agent can be administered about 1 hour, about 2 hours, about 3 hours, about 4 hours, about 5 hours, about 6 hours, about 12 hours, about 24 hours, about 48 hours, about 72 hours, or longer prior to administration of the carrier protein-bound chemotherapeutic/binding agent complex. In other embodiments, the binding agent can be administered about 1 day, about 2 days, about 3 days, about 4 days, about 5 days, about 6 days, about 7 days, about 10 days, about 12 days, about 15 days, or longer prior to administration of the carrier protein-bound chemotherapeutic/binding agent complex.

In some embodiments, the binding agent can be administered concurrently with administration of the carrier protein-bound chemotherapeutic/binding agent complex, for example, within 10 minutes or less of each other. In other embodiments, the binding agent can be administered subsequent to administration of the carrier protein-bound chemotherapeutic/binding agent complex, for example, within 2 hours after administration of the carrier protein-bound chemotherapeutic/binding agent complex, provided that the subsequent administration allows the antibody to preferentially bind the soluble antigen.

In some embodiments, the sub-therapeutic amount of binding agent is selected from an amount consisting of about 1%, about 5%, about 10%, about 15%, about 20%, about 25%, about 30%, about 35%, about 40%, about 45%, about 50%, about 55% or about 60% of the therapeutic dosage of the binding agent.

In some embodiments, the sub-therapeutic amount of anti-VEGF antibody is an amount which preferentially blocks circulating VEGF without blocking VEGF associated with tumor.

In one aspect, the anti-antigen (e.g., anti-soluble antigen, e.g., anti-VEGF) dose is a unit-dose formulation of an anti-antigen binding agent which formulation comprises from about 1% to about 60% of a therapeutic dose of said binding agent wherein said formulation is packaged so as to be administered as a unit dose. In an aspect, the unit-dose formulation of an anti-antigen binding agent comprises about 10% of a therapeutic dose of said binding agent. For example 10% of a therapeutic dose of an anti-VEGF antibody, e.g., bevacizumab, may be 0.5 mg/kg to 5 mg/kg.

The unit-dose formulation of an anti-antigen (e.g., anti-soluble antigen, e.g., anti-VEGF) binding agent can be about 1% to about 60%, about 5% to about 50%, about 10% to about 40%, about 15% to about 30%, about 20% to about 25%, of a therapeutic dose of the anti-antigen (e.g., anti-soluble antigen, e.g., anti-VEGF) binding agent. Contemplated values include any value, subrange, or range within any of the recited ranges, including endpoints.

In some embodiments, the anti-antigen (e.g., anti-soluble antigen, e.g., anti-VEGF) antibody is a biosimilar version thereof (e.g., a biosimilar version of bevacizumab), which formulation comprises from about 5% to about 20% of a therapeutic dose of the antibody or a biosimilar version thereof.

Kits

In some aspects, provided herein are kits comprising: (a) an amount of a carrier protein-bound chemotherapeutic/anti-antigen binding agent complexes, and optionally (b) instructions for use. In some embodiments, provided herein are kits comprising: (a) an amount of a carrier protein-bound chemotherapeutic/anti-antigen binding agent complexes, (b) a unit dose of a sub-therapeutic amount of anti-antigen binding agent, and optionally (c) instructions for use. In some embodiments, the kits can include lyophilized complexes of the carrier protein-bound chemotherapeutic/binding agent.

In some embodiments, the kit components can be configured in such a way that the components are accessed in their order of use. For example, in some aspects the kit can be configured such that upon opening or being accessed by a user, the first component available is the unit dose of a sub-therapeutic amount of binding agent, for example, in a first vial. A second container (e.g., a vial) comprising or containing an amount of the carrier protein-bound chemotherapeutic/binding agent complexes can then be accessed. As such the kits can be intuitively configured in a way such that the first vial must be opened prior to the second vial being opened. It should be understood that in some embodiments, the order can be different, for example, where it is desired to administer the complex first, prior to the administration of the binding agent. Also, it can be configured such that both are administered at the same time. Finally, it should be understood that additional vials or containers of either or both component(s) can be included, and configured for opening in any desired order. For example, the first vial could be binding agent, the second vial could include complex, a third could include either binding agent or complex, etc. It is contemplated that a kit configured in such a way would prevent, or at least help to prevent, the components from being administered in an order not intended by the instructions for use.

In some aspects, the invention is directed to a kit of parts for administration of carrier protein-bound chemotherapeutic/anti-antigen (e.g., anti-soluble antigen, e.g., anti-VEGF) binding agent complexes and a unit dose of a sub-therapeutic amount of binding agent; and optionally further comprising a dosing treatment schedule in a readable medium. In some embodiments, the dosing schedule includes the sub-therapeutic amount of anti-soluble antibody required to achieve a desired average serum level is provided. In some embodiments, the kit of parts includes a dosing schedule that provides an attending clinician the ability to select a dosing regimen of the sub-therapeutic amount of anti-soluble binding agent based on the sex of the patient, mass of the patient, and the serum level that the clinician desires to achieve. In some embodiments, the dosing treatment is based on the level of circulating soluble antigen (e.g., VEGF) in the blood of the patient. In some embodiments, the dosing schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

List of Sequences

| LIST OF SEQUENCES |
|---|
| anti-PDL1 H6B1L-EM (STI3031) IgG1 antibody heavy chain SEQ ID NO: 1:<br>QMQLVQSGAEVKKPGSSVKVSCKASGGTFSSYAYSWVRQAPGQGLEWMG<br>GIIPSFGTANYAQKFQGRVTITADESTSTAYMELSSLRSEDTAVYYCAR<br>GPIVATITPLDYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISKA<br>KGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHYT<br>QKSLSLSPGK |
| anti-PDL1 H6B1L-EM (STI3031) lambda antibody light chain SEQ ID NO: 2:<br>SYVLTQPPSVSVAPGKTATIACGGENIGRKTVHWYQQKPGQAPVLVIYY<br>DSDRPSGIPERFSGSNSGNTATLTISRVEAGDEADYYCLVWDSSSDHRI<br>FGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSCQ<br>VTHEGSTVEKTVAPTECS |

EXAMPLES

The foregoing examples are illustrative of the present invention, and are not to be construed as limiting thereof. Although the invention has been described in detail with reference to preferred embodiments, variations and modifications exist within the scope and spirit described herein as described and defined in the following claims.

Example 1 Manufacturing Drug Containing Nanoparticles

SN38-Nab or SN38-NTP Nab (nanoparticle albumin bound SN38) 30 mg of SN38 was dissolved in 0.6 ml DMSO, and 10 mg of paclitaxel (or non-toxic paclitaxel (NTP) derivative (20-acetoxy-4-deacetyl-5-epi-20, O-secotaxol)) was dissolved in 0.5 ml chloroform. The two solutions were mixed, and 0.1 ml ethanol was added to the mixture. 400 mg of human serum albumin (HSA) was dissolved in 38.8 ml HPLC grade water, added to the drug mixture and homogenized with a hand-held homogenizer at 5000 rpm for 5 minutes. The homogenized mixture was then added to a Microfluidics microfluidizer high pressure emulsifier (Microfluidizer Model 110S) and pumped through the tubing 20 times, forming nanoparticle albumin-bound SN38 (SN38-Nab or SN38-NTP Nab). The nanoparticle mixture was frozen at −80° C. overnight and lyophilized for 96 hours. The nanoparticles were reconstituted at 100 mg/ml of saline solution.

DOX-Nab or DOX-NTP Nab (Nanoparticle Albumin Bound Doxorubicin)

Step 1: Doxorubicin hydrochloride is converted to hydrophobic form—50 mg of doxorubicin-HCl (Caymab Chemical, Cat #15007) was dissolved in 12 ml:8 ml mixture of chloroform:methanol (3:2), followed by addition of 112 mg triethylamine (Acros Organics, Cat #15791). The solution was mixed by rotation for 24 hours at room temperature. The solution was then evaporated by rotavapor for 5 minutes at 40° C. without allowing the doxorubicin to dry. This process was repeated 3-4 times until all the solvents were removed. The doxorubicin was resuspended in 7.5-10 ml chloroform.

Step 2: 30 mg doxorubicin was dissolved in about 6 ml chloroform. 10 mg of paclitaxel (or non-toxic paclitaxel (NTP) derivative (20-acetoxy-4-deacetyl-5-epi-20, O-secotaxol)) was dissolved in the doxorubicin solution and 10% volume of 100% ethanol was added. 400 mg of human serum albumin (HSA) was dissolved in 34 ml HPLC grade water, added to the drug mixture and stirred for 5 minutes. Immediately after mixing, the mixture was transferred to a glass reservoir and emulsified using Microfluidizer pump. The mixture was pumped through the tubing system 20 times at 80 to 100 psi. Every $5^{th}$ time through the pump the system was closed to allow the mixture to circulate through the pump tubing 5 times. The nanoparticle mixture was then evaporated by rotavapor for 25 minutes at 40° C. The mixture was frozen at −80° C. for at least 4 hours and then lyophilized for 48-72 hours. The nanoparticles were reconstituted at 100 mg/ml of saline solution.

Nano-Immune Conjugate (NIC)

The antibody was incubated with SN38-Nab, SN38-NTP Nab, DOX-Nab or DOX-NTP Nab at a ratio of 1:25 (antibody:nanoparticle by concentration) in 0.9% saline for 30-60 minutes at room temperature with gentle agitation.

Example 2 Stability and Cytotoxicity of Doxorubicin/Pactilaxel Nanoparticles

The present inventors previously have developed nanoparticle complexes comprising 130 nm nanoparticles that contains paclitaxel in the center of sphere of human serum albumin that have the ability to bind clinically relevant monoclonal antibodies, including bevacizumab, rituximab, and atezolizumab among others, creating a 160 nm particle. The complexes have been shown to have clinical efficacy. Data suggest that the improved clinical efficacy of the antibody coated nanoparticle relative to the nanoparticle alone is at least in part due to altered biodistribution, which favors higher drug deposition away from circulation and into the tumor.

Although other hydrophobic small molecules can form a stable nanoparticle with albumin, paclitaxel is uniquely capable of opening the antibody binding sites on the albumin. In order to include other chemotherapy agents in the hydrophobic pocket within the center of the albumin, doxorubicin and SN38 were tested in various ratios with paclitaxel (TAXOL®) to make stable nanoparticles, which were also able to non-covalently bind cancer targeting antibodies.

These doxorubicin containing nanoparticles demonstrated improved stability relative to the paclitaxel only nanoparticles. This added particle stability may further improve biodistribution to favor drug deposition in the tumor and further increase clinical efficacy. Nanosight was performed to determine the particle size of nanoparticles made with doxorubicin and paclitaxel (TAXOL®) in a 1:1, 1:3 and 1:9 ratio by weight (FIG. 1A). These data suggest that nanoparticles made with both doxorubicin and paclitaxel (TAXOL®) form stable particles that are all a similar size. After manufacturing of the doxorubicin and paclitaxel (TAXOL®) nanoparticles, measurements were taken of total and albumin bound drug by HPLC. Nanosight measurements were taken to determine the concentration at which the nanoparticles are no longer stable. Particles containing doxorubicin were stable and measurable at much higher dilutions than nanoparticles with paclitaxel (TAXOL®) alone.

Figure 2:
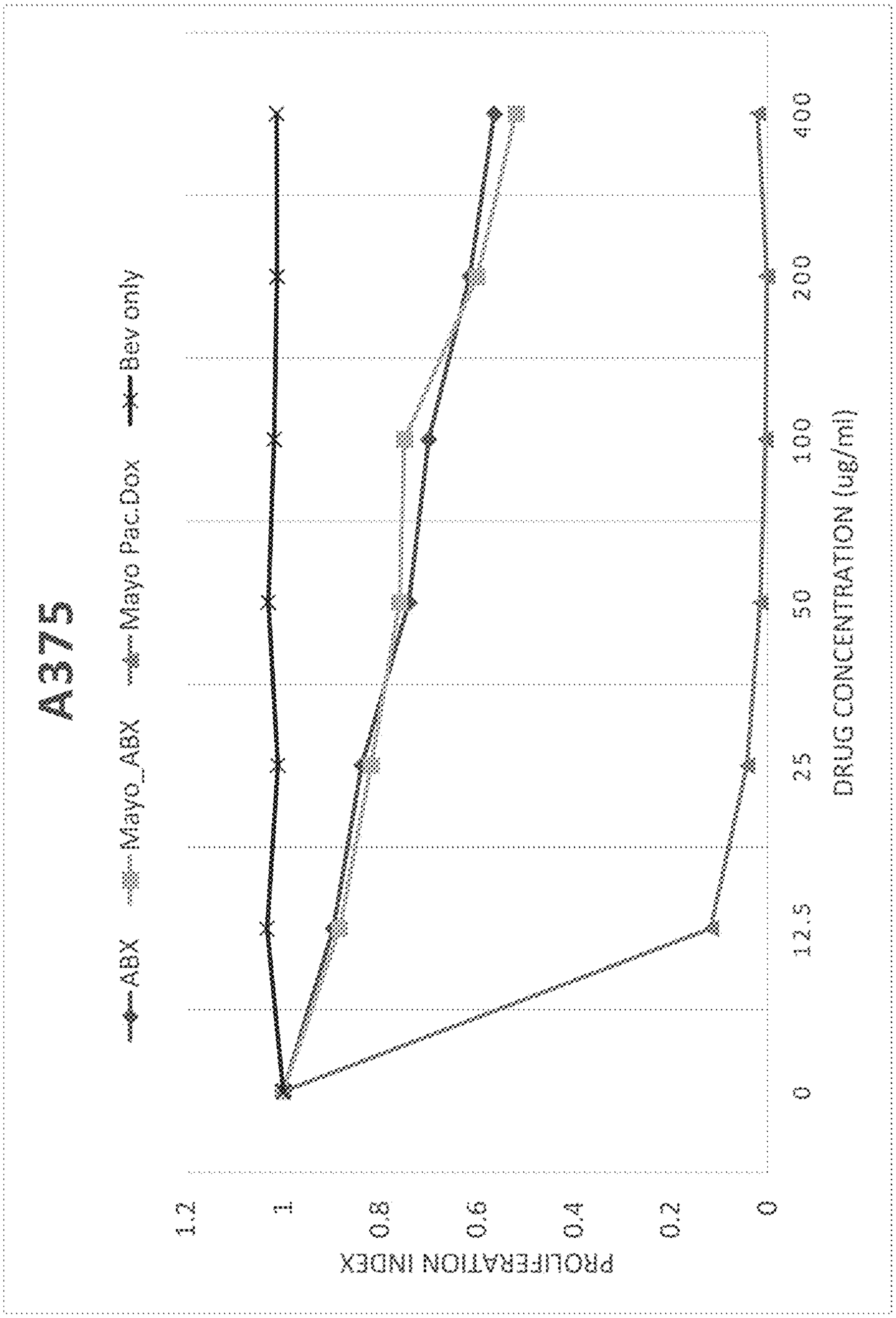
FIG. 2 shows the toxicity of the nanoparticles on A375 cells relative to bevacizumab, ABRAXANE®, and nab-paclitaxel.

The cytotoxicity of albumin particles containing a 1:1 ratio of doxorubicin:paclitaxel (inventor manufactured nanoparticle complexes; Mayo_Pac.Dox), commercial ABRAXANE® (Com_ABX), nab-paclitaxel (inventor manufactured Abraxane; Mayo_ABX), and commercial bevacizumab (Avastin, Bev only) was tested against A375 melanoma cells. Mayo_ABX was prepared according to procedure described above for preparation of DOX-Nab, but without the doxorubicin. 6.25 to 200 mg/ml of each paclitaxel and doxorubicin were combined with human serum albumin (HSA) to form nanoparticles containing both chemotherapy drugs Mayo_Pac.Dox (which were prepared according to procedure for preparation of DOX-Nab above). $7.5\times10^4$ A375 cells were plated in each well of a 24 well plate in DMEM media with 10% fetal calf serum (FCS). A375 cells were incubated overnight at 37° C. and 5% $CO_2$ with 12.5 to 400 mg/ml bevacizumab, 12.5 to 400 mg/ml commercial ABRAXANE®, 12.5 to 400 mg/ml inventor-manufactured nab-paclitaxel, or doxorubicin:paclitaxel nanoparticles (6.25 to 200 mg/ml of each paclitaxel and doxorubicin), 10 mM of 5-Ethynyl-2'-deoxyuridine (EdU) was also included in each well. After the overnight incubation, the cells were harvested and fixed in 4% paraformaldehyde. After fixation, the cells are permeabilized with detergent (10% saponin) and stained with Alexa Fluor 647 conjugated anti-EdU antibody as per manufacturer's instructions (Invitrogen, Cat #C10634). Enumeration of Alexa Fluor 647 positive, proliferating cells was done by flow cytometry (Guava 8HT, Millipore). FIG. 2 shows the concentration of the drug in the nanoparticles (X-axis) vs. proliferation index of A375 cells (Y-axis). The proliferation index was calculated by dividing the percent positive in the test wells by percent positive in the untreated (maximum proliferation), EdU labeled cells. The doxorubicin:paclitaxel nanoparticles (Mayo_Pac.Dox) were significantly more toxic than nanoparticles containing paclitaxel only with most cells being dead at just 12.5 μg/ml of drug.

Example 3 Characterization of Doxorubicin/Paclitaxel Derivative and SN38/Paclitaxel Derivative Nanoparticles In the following experiment non-toxic form of paclitaxel (NTP) was used for manufacturing some of the nanoparticles, instead of the regular paclitaxel (FIG. 3), in order to isolate the toxic effects of SN38 or doxorubicin from that of paclitaxel in the nanoparticles. Doxorubicin and SN38 were tested in various ratios with the non-toxic paclitaxel derivative (20-acetoxy-4-deacetyl-5-epi-20, O-secotaxol) to make stable nanoparticles, which were also able to bind cancer targeting antibodies non-covalently.

Figure 4A:
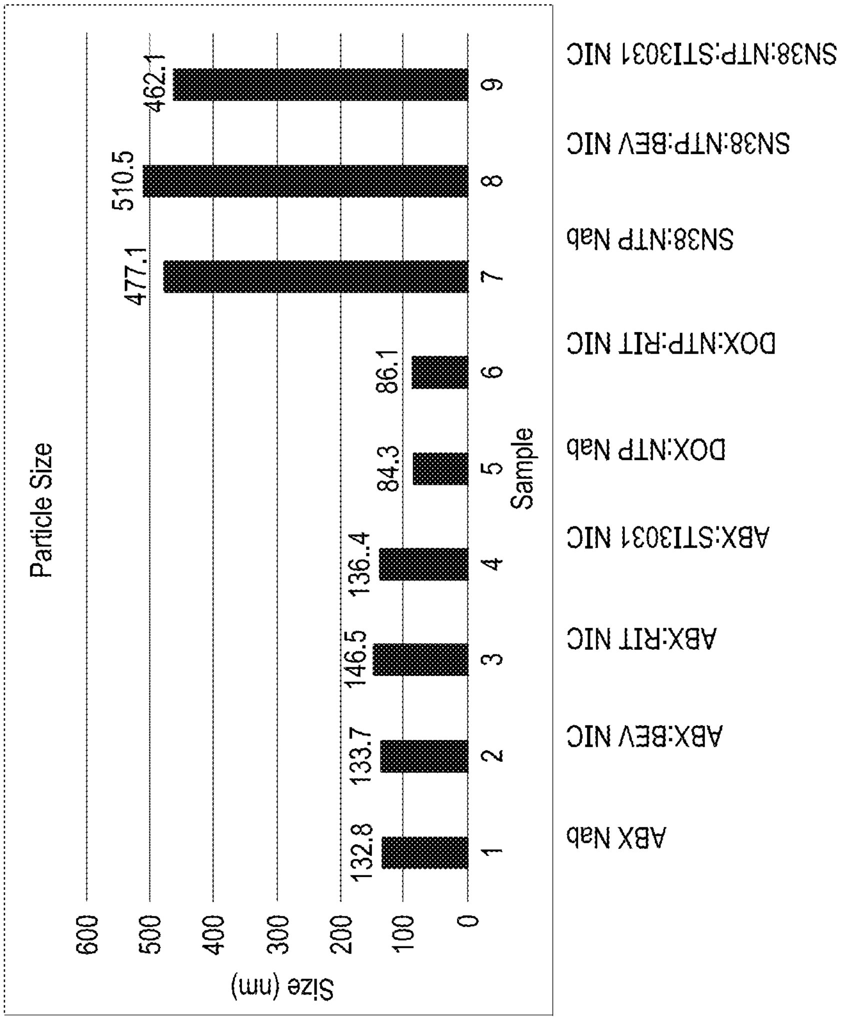
FIG. 4A shows the particle size of the following nanoparticles: ABX Nab, ABX:BEV NIC, ABX:RIT NIC, ABX:STI3031 NIC, DOX:NTP Nab, DOX:NTP:RIT NIC, SN38:NTP Nab, SN38:NTP:BEV NIC, and SN38:NTP:STI3031 NIC.

Nanosight was performed to determine the particle size of the following nanoparticles: ABX Nab (commercial ABRAXANE®), ABX:BEV NIC (ABRAXANE® nanoparticles conjugated with bevacizumab), ABX:RIT NIC (ABRAXANE® nanoparticles conjugated with rituximab), ABX:STI3031 NIC (ABRAXANE® nanoparticles conjugated with PDL1 antibody STI3031), DOX:NTP Nab (nab-paclitaxel nanoparticles, using non-toxic paclitaxel derivative, with doxorubicin), DOX:NTP:RIT NIC (nab-paclitaxel nanoparticles, using non-toxic paclitaxel derivative, with doxorubicin and conjugated with rituximab), SN38:NTP Nab (nab-paclitaxel nanoparticles, using non-toxic paclitaxel derivative, with SN38), SN38:NTP:BEV NIC (nab-paclitaxel nanoparticles, using non-toxic paclitaxel derivative, with SN38 and conjugated with bevacizumab), SN38:NTP:STI3031 NIC (nab-paclitaxel nanoparticles, using non-toxic paclitaxel derivative, with SN38 and conjugated with PDL1 antibody STI 3031) (FIG. 4A). These data suggest that nanoparticles made with both doxorubicin and non-toxic paclitaxel derivative (NTP) (20-acetoxy-4-deacetyl-5-epi-20, O-secotaxol) form particles that are all a similar size and smaller than nanoparticles without doxorubicin, whereas nanoparticles made with both SN38 and non-toxic paclitaxel derivative form particles that are all a similar size and much larger than nanoparticles without SN38.

Figure 4B:
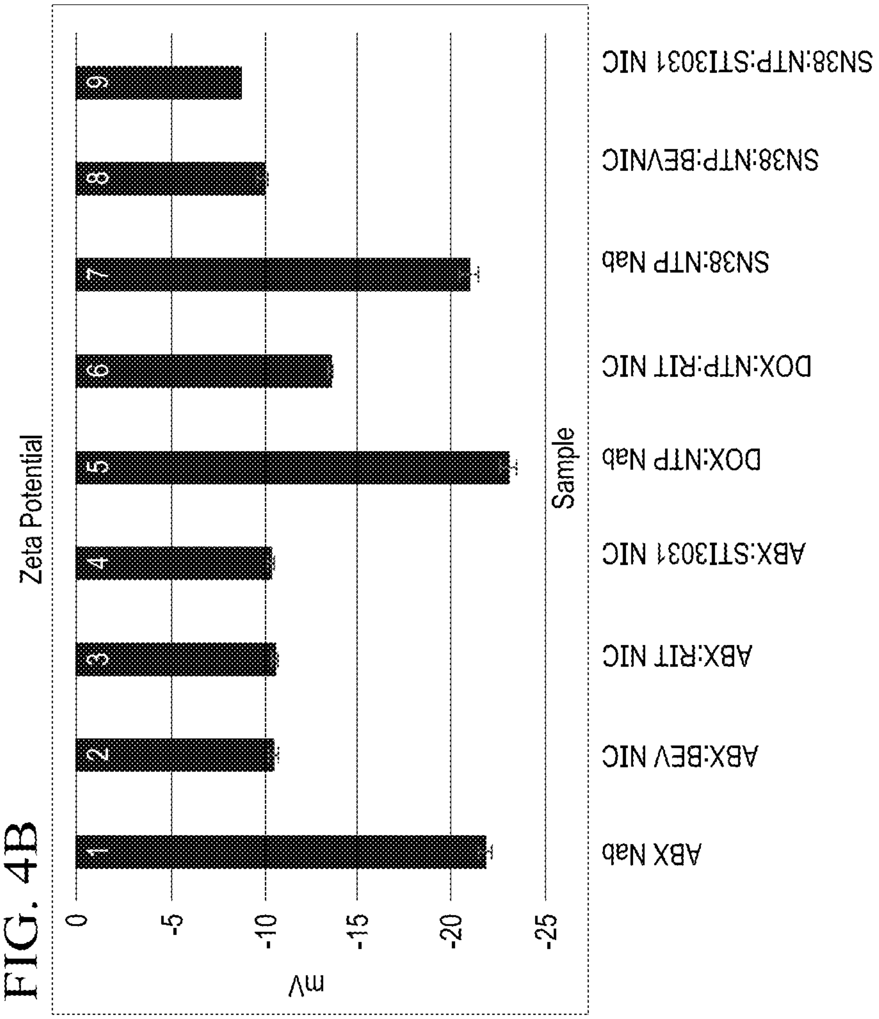
FIG. 4B shows Zeta potential of the following nanoparticles: ABX Nab, ABX:BEV NIC, ABX:RIT NIC, ABX:STI3031 NIC, DOX:NTP Nab, DOX:NTP:RIT NIC, SN38:NTP Nab, SN38:NTP:BEV NIC, and SN38:NTP:STI3031 NIC.
Figure 4C:
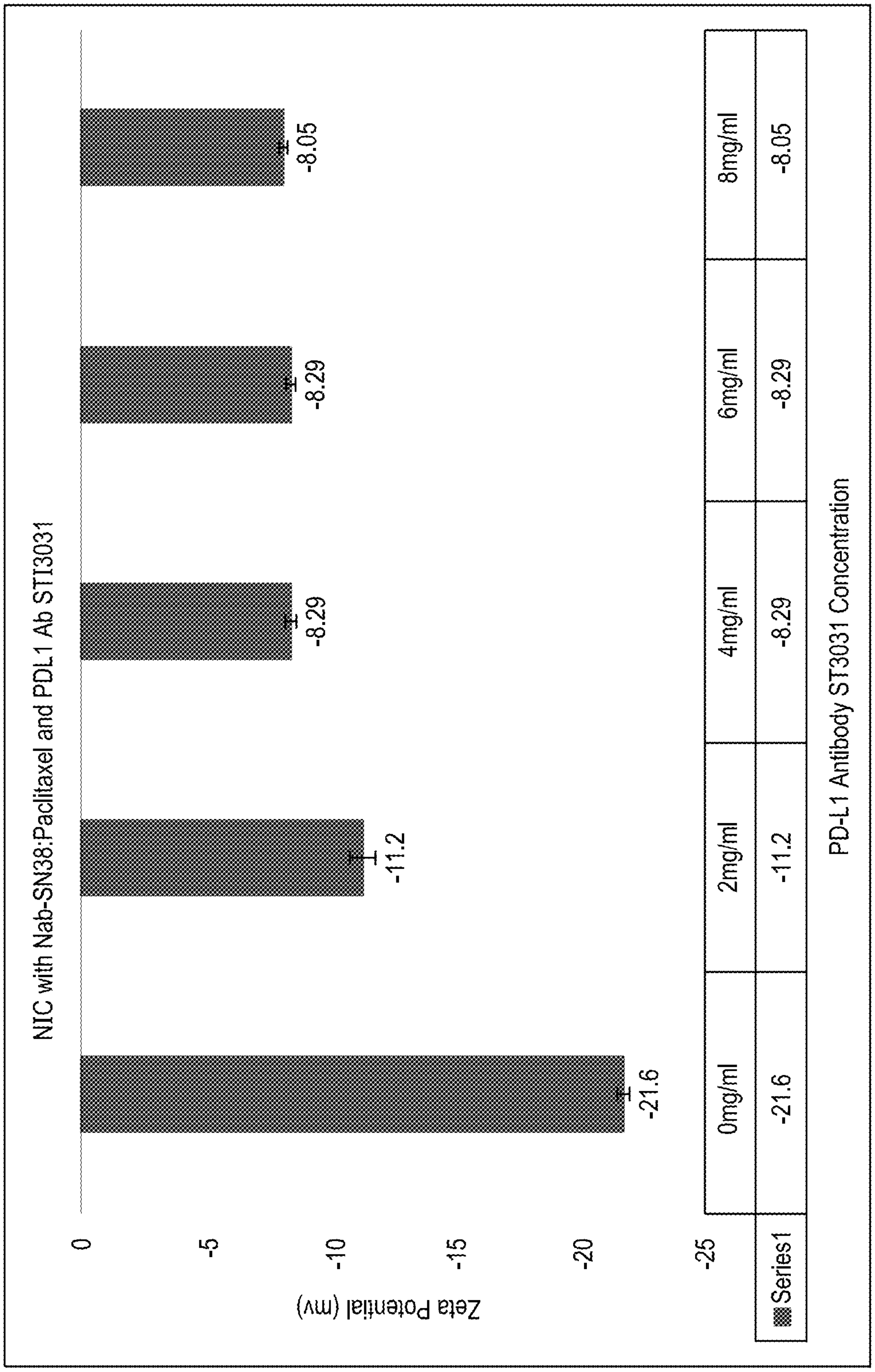
FIG. 4C shows Zeta potential of nab-paclitaxel nanoparticles with SN38 alone or conjugated with 2 mg/ml, 4 mg/ml, 6 mg/ml, or 8 mg/ml PDL1 antibody (STI-3031).

Zeta potential of the particles described in the paragraph above was measured using Zetasizer (Malvern). The data suggests that including doxorubicin in the nanoparticles slightly decreases zeta potential, whereas SN38 does not affect it. Conjugating antibodies with the nanoparticles, significantly increases zeta potential (FIG. 4B). The increase in zeta potential was used to confirm that the antibodies bound to the surface of the nanoparticles. FIG. 4C shows the zeta potential of nano-immune conjugates (NICs) made from nab-paclitaxel (TAXOL®) nanoparticles with SN38 and conjugated with various concentrations of STI3031 (PDL1) antibody. Zeta potential increases with increase in the concentration of STI3031 antibody conjugated to the nab-paclitaxel SN38 nanoparticles, and appears to reach its maximum when 4 mg/ml antibody is conjugated with nab-paclitaxel SN38 nanoparticles.

Example 4 Drug Loading and Binding Efficiency

Figure 5A:
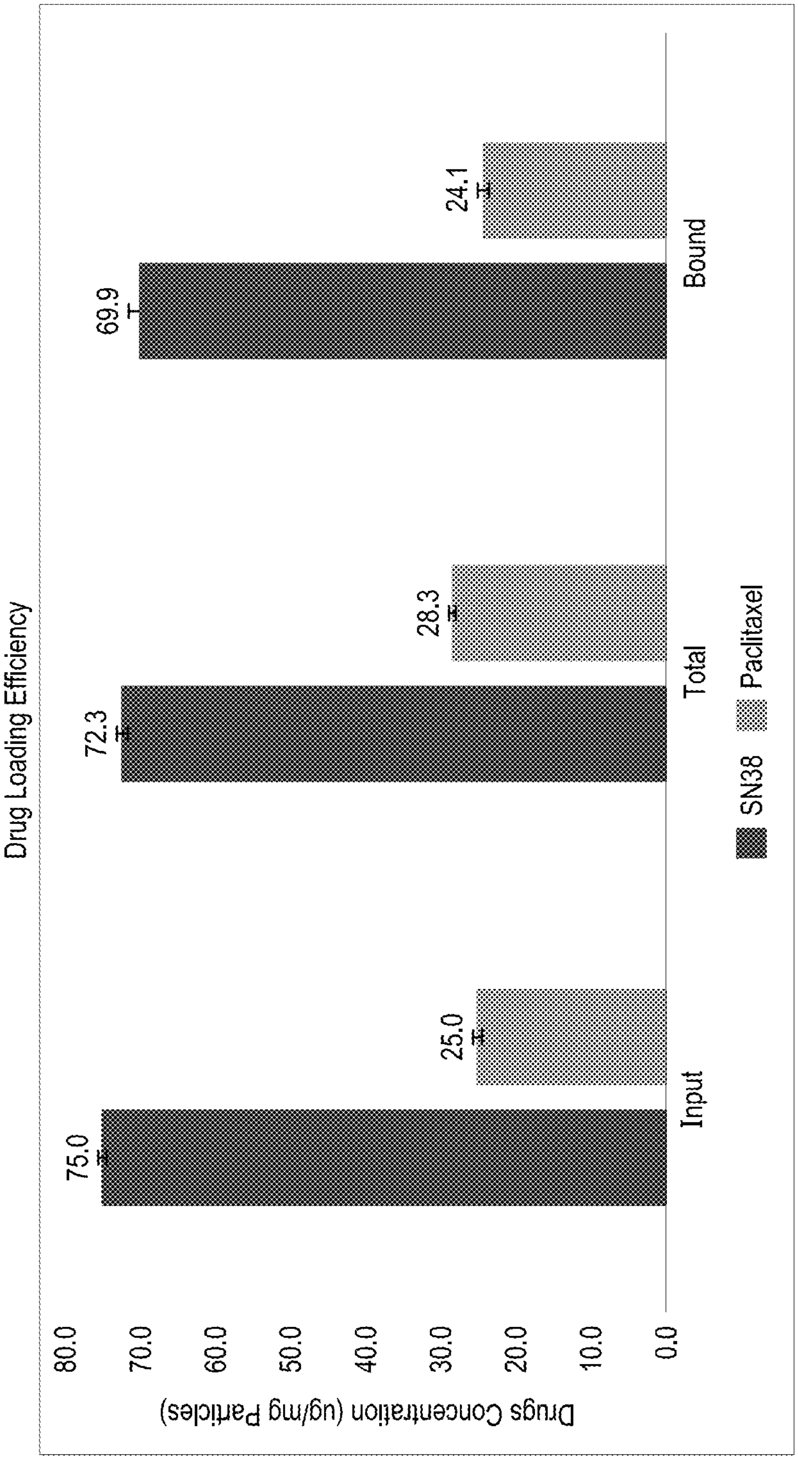
FIG. 5A shows the original input of SN38 and non-toxic paclitaxel, and total and albumin bound drug after manufacture of the nanoparticles as measured by HPLC.

After manufacturing of the SN38 and paclitaxel (TAXOL®) nanoparticles, measurements were taken of total and albumin bound drug by HPLC (FIG. 5A). The data suggests that SN38 has very good loading and binding efficiency. When 75.0 mg SN38 and 25 mg paclitaxel (TAXOL®) were homogenized and emulsified with albumin to prepare the nanoparticles, a total of 72.3 mg of SN38 were detected (96.4% loading efficiency) and 69.9 mg of SN38 were non-covalently bound to the nanoparticles (96.7% binding efficiency).

Figure 5B:
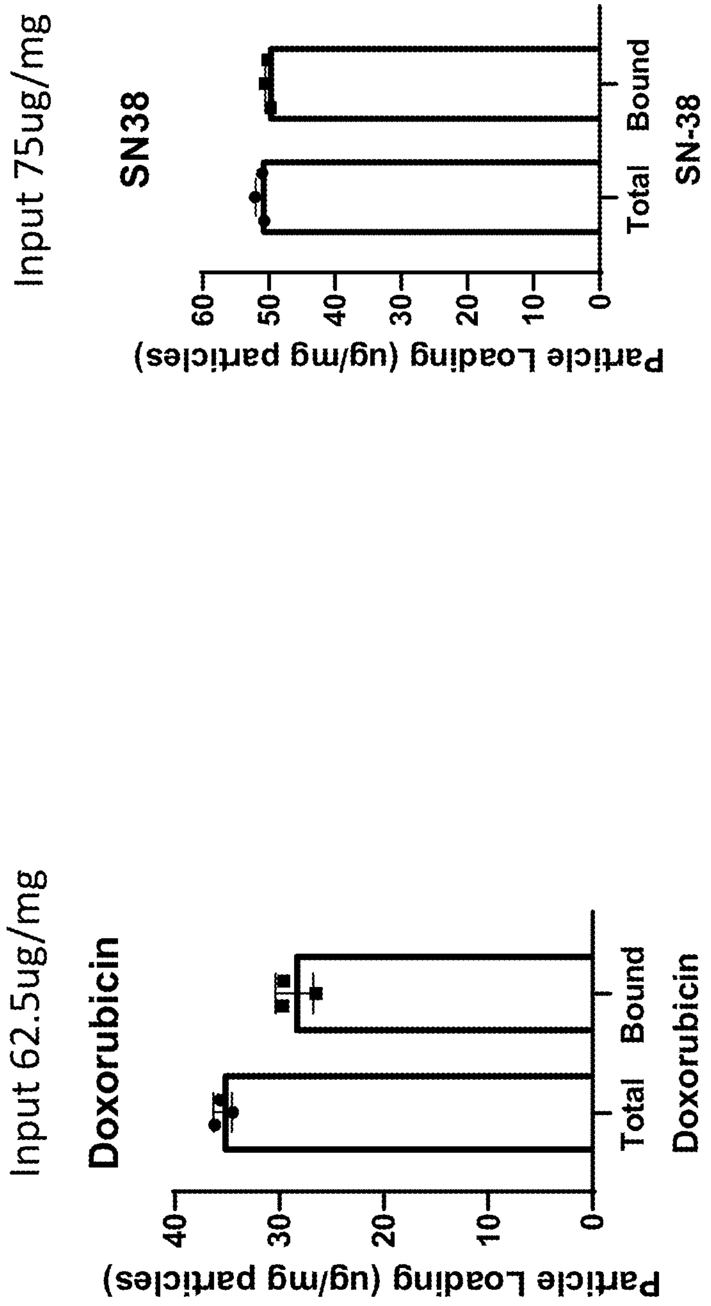
FIG. 5B shows the total and albumin bound drug (SN38 or doxorubicin) after manufacture of the nanoparticles as measured by HPLC (non-toxic paclitaxel was used to manufacture the nanoparticles).

After manufacturing of the doxorubicin and non-toxic paclitaxel derivative (NTP) nanoparticles or SN38 and non-toxic paclitaxel derivative (NTP) nanoparticles, measurements were taken of total and albumin bound drug by HPLC (FIG. 5B). When 62.5 mg doxorubicin, non-toxic paclitaxel derivative and albumin were homogenized and emulsified together to form nanoparticles, a total of 35 mg doxorubicin were detected (56% loading efficiency) and about 27.5 mg doxorubicin were non-covalently bound to the nanoparticles (78.6% binding efficiency). When 75 mg SN38, non-toxic paclitaxel derivative and albumin were homogenized and emulsified together to form nanoparticles, a total of 51.2 mg SN38 were detected (68.2% loading efficiency) and about 50.1 mg SN38 were non-covalently bound to the nanoparticles (97.9% binding efficiency). The data suggests that SN38 has much better loading and binding efficiency than doxorubicin.

Figure 6A:
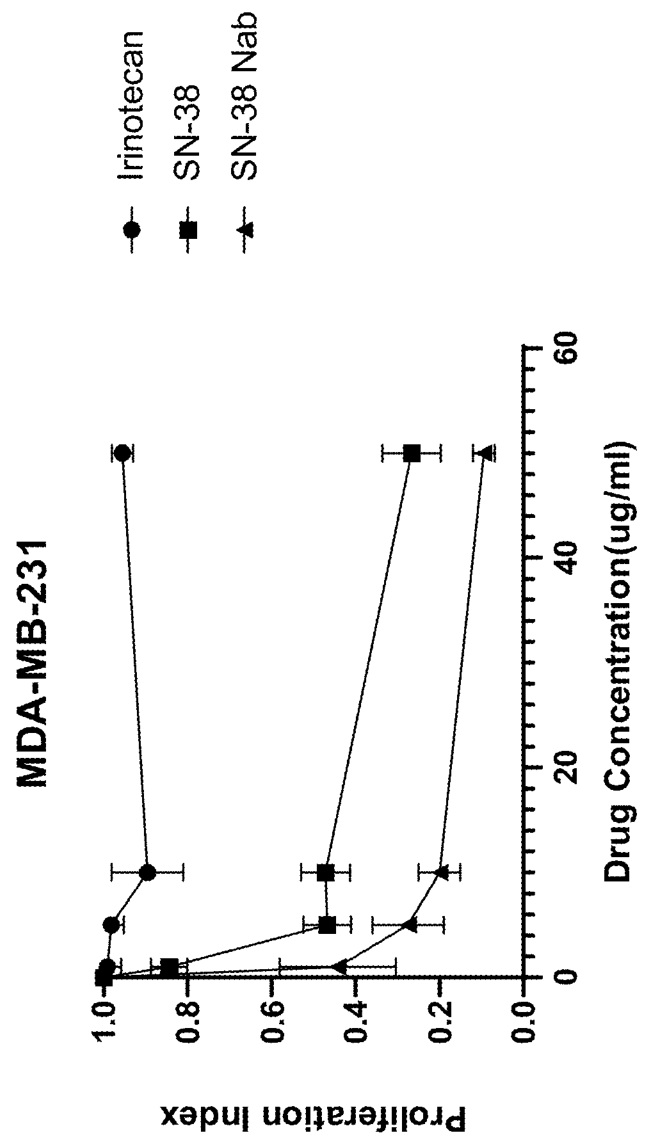
FIG. 6A shows the toxicity of the SN38 Nab nanoparticles (nab-paclitaxel nanoparticles with SN38) on MDA-MB-231 cells relative to irinotecan and SN38 (non-toxic paclitaxel was used to manufacture the nanoparticles).

Example 5 Cytotoxicity of Doxorubicin/Non-Toxic Paclitaxel and SN38/Non-Toxic Paclitaxel Nanoparticles The cytotoxicity of irinotecan (a topoisomerase I inhibitor used to treat several cancer types), SN38 (hydrophobic active metabolite of irinotecan), and SN38 Nab (where non-toxic paclitaxel derivative was used to prepare the nanoparticles as described above) was tested against MDA-MB-231 breast cancer cells. $1\times10^5$ MDA-MB-231 cells were plated in each well of a 24 well plate in DMEM media with 10% fetal calf serum (FCS). MDA-MB-231 cells were incubated overnight at 37° C. and 5% $CO_2$ with 1, 5, 10, or 50 mg/ml of irinotecan, SN38, or SN38 Nab nanoparticles, and 10 mM of 5-Ethynyl-2'-deoxyuridine (EdU) was also included in each well. After the overnight incubation, the cells were harvested and fixed in 4% paraformaldehyde. After fixation, the cells are permeabilized with detergent (10% saponin) and stained with Alexa Fluor 647 conjugated anti-EdU antibody as per manufacturer's instructions (Invitrogen, Cat #C10634). Enumeration of Alexa Fluor 647 positive, proliferating cells was done by flow cytometry (Guava 8HT, Millipore). FIG. 6A shows the concentration of the drug in the nanoparticles (X-axis) vs. proliferation index of MDA-MB-231 cells (Y-axis). The proliferation index was calculated by dividing the percent positive in the test wells by percent positive in the untreated (maximum proliferation), EdU labeled cells. The SN38 Nab nanoparticles were significantly more toxic than SN38 and irinotecan with more than half the cells being dead at just 1 μg/ml of drug. Importantly, there was no loss of toxicity of SN38, at any concentration, as a result of inclusion of the drug in the nanoparticles.

Figure 6B:
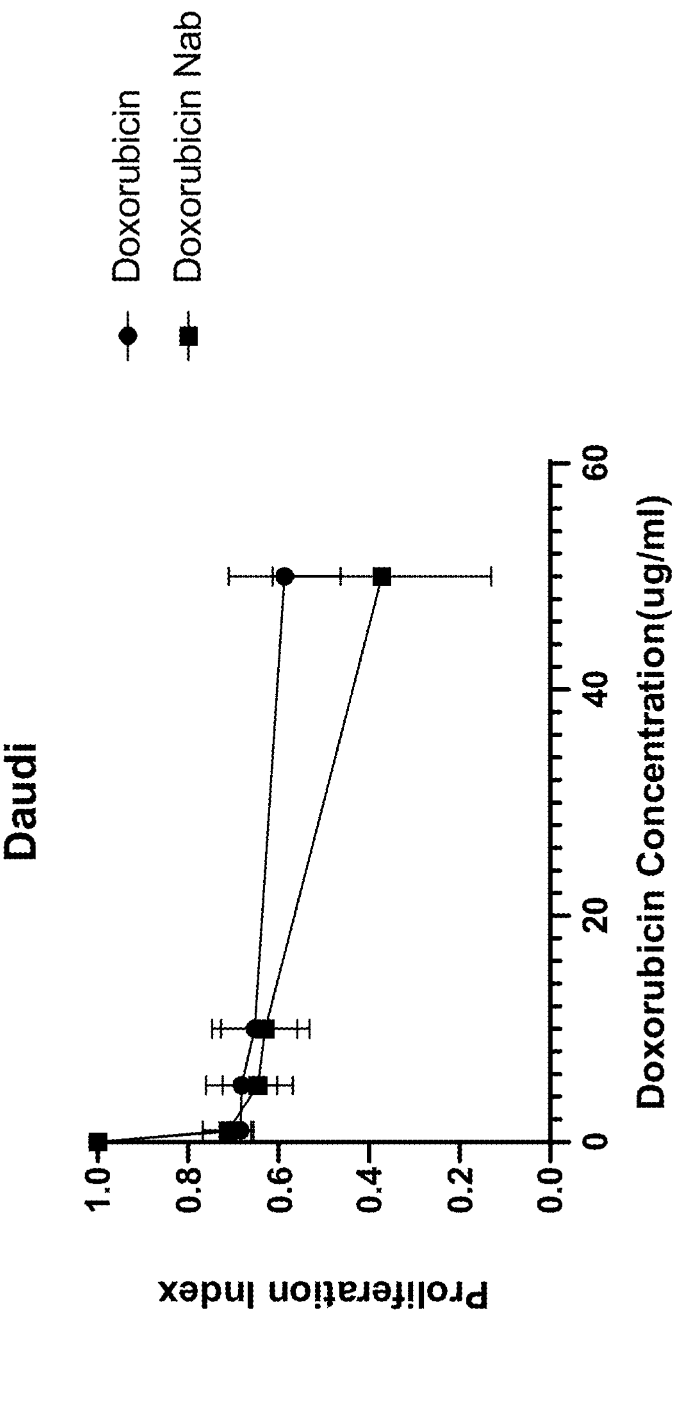
FIG. 6B shows the toxicity of the doxorubicin Nab nanoparticles (nab-paclitaxel nanoparticles with doxorubicin) on Daudi cells relative to doxorubicin (non-toxic paclitaxel was used to manufacture the nanoparticles).
Figure 7A:
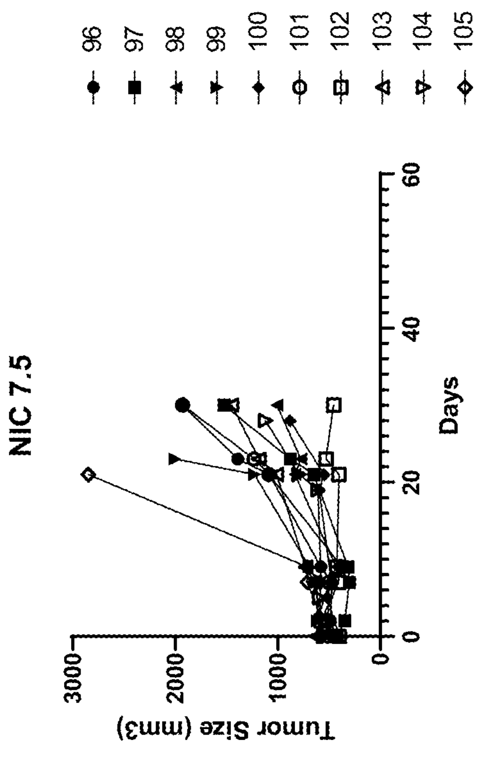
FIG. 7A shows in vivo efficacy of NIC 7.5 (nab-paclitaxel nanoparticles with 7.5 mg/kg of SN38 and conjugated to PDL1 antibody STI 3031) in mice.
Figure 7B:
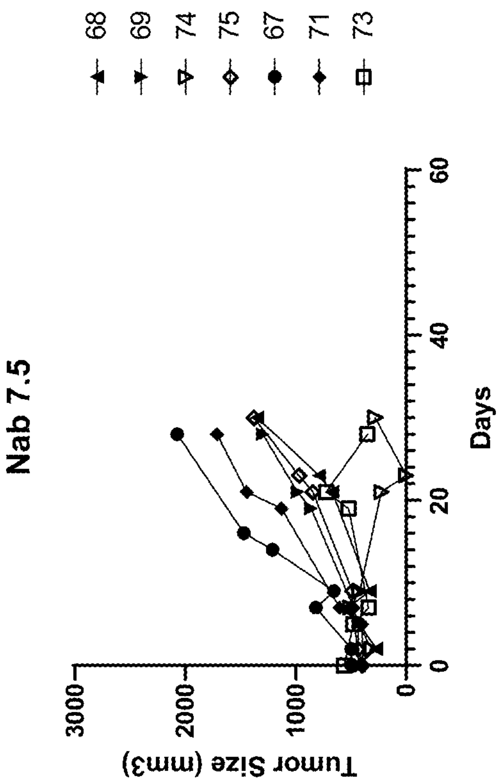
FIG. 7B shows in vivo efficacy of Nab 7.5 (nab-paclitaxel nanoparticles with 7.5 mg/kg of SN38) in mice.
Figure 7D:
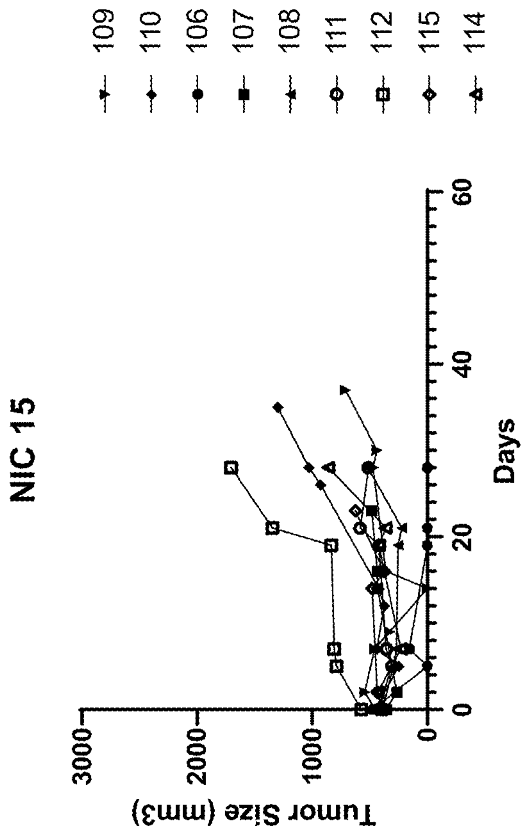
FIG. 7D shows in vivo efficacy of NIC 15 (nab-paclitaxel nanoparticles with 15 mg/kg of SN38 and conjugated to PDL1 antibody STI 3031) in mice.
Figure 7C:
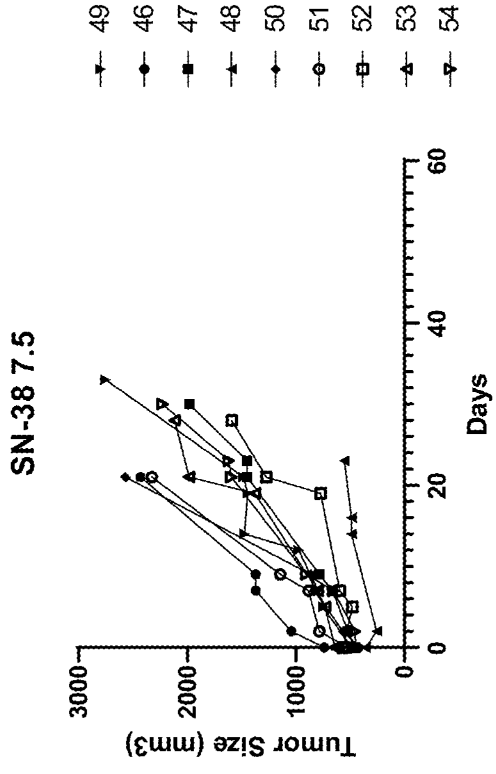
FIG. 7C shows in vivo efficacy of SN38 7.5 (7.5 mg/kg of SN38) in mice.
Figure 7E:
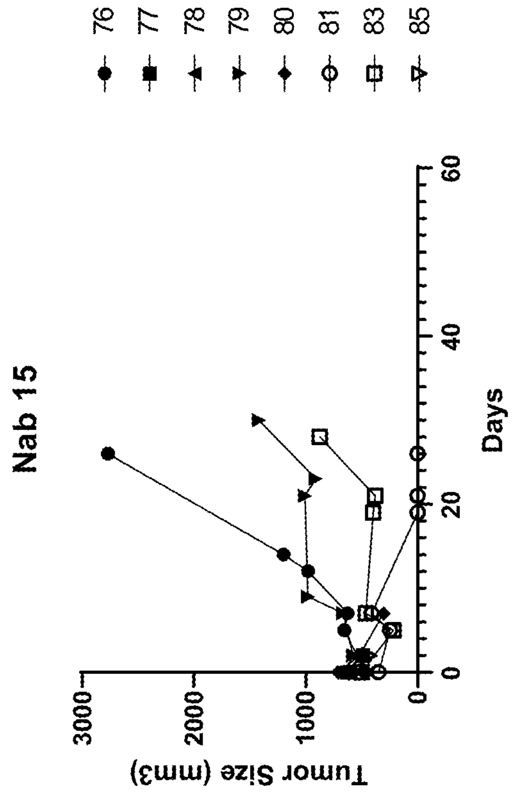
FIG. 7E shows in vivo efficacy of Nab 15 (nab-paclitaxel nanoparticles with 15 mg/kg of SN38) in mice.
Figure 7F:
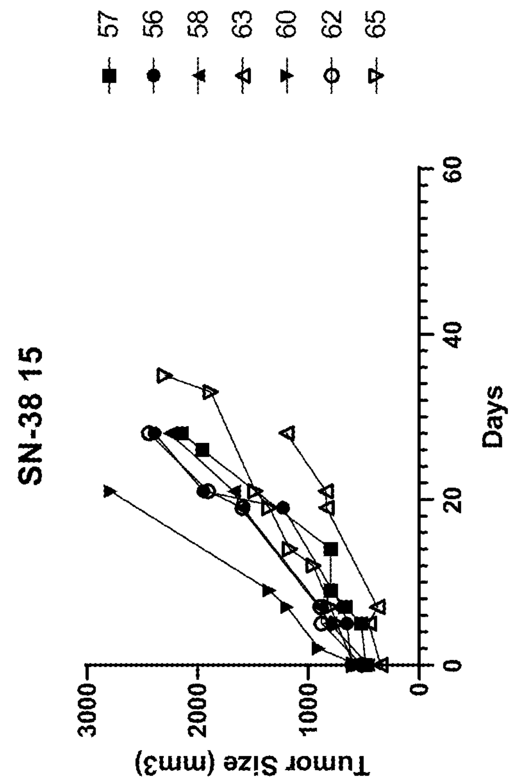
FIG. 7F shows in vivo efficacy of SN38 15 (15 mg/kg of SN38) in mice.
Figure 7G:
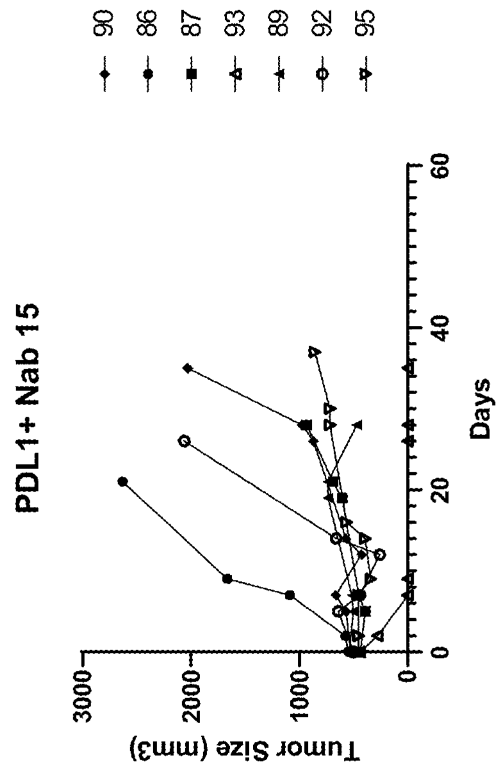
FIG. 7G shows in vivo efficacy of PDL1+Nab 15 (nab-paclitaxel nanoparticles with 15 mg/kg of SN38 and separately injected PDL1 antibody STI 3031) in mice.
Figure 7H:
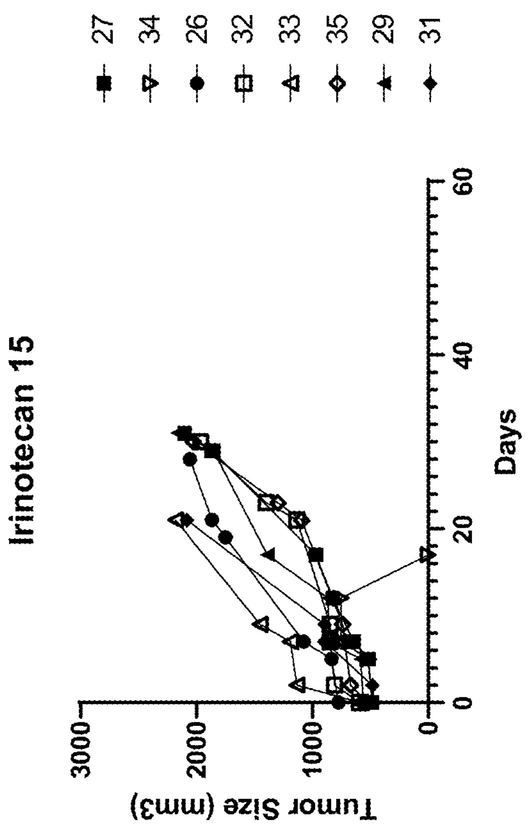
FIG. 7H shows in vivo efficacy of Irinotecan 15 (15 mg/kg of Irinotecan) in mice.
Figure 7J:
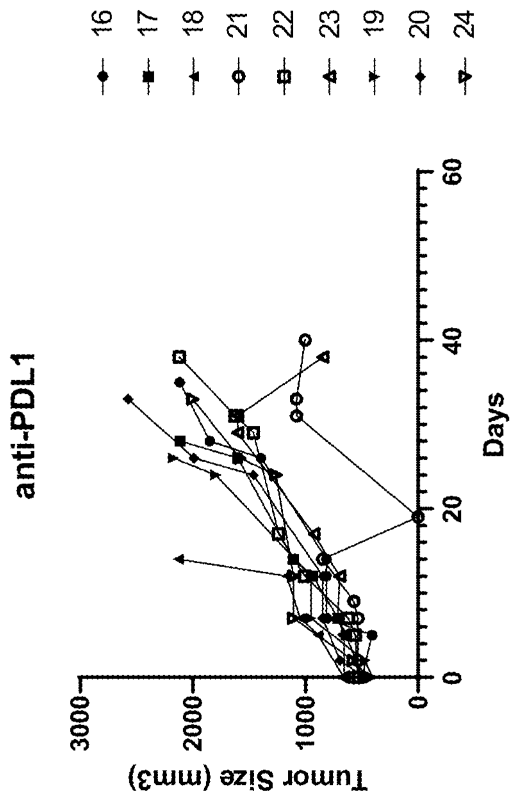
FIG. 7J shows in vivo efficacy of anti-PDL1 antibody (STI3031) in mice.
Figure 7I:
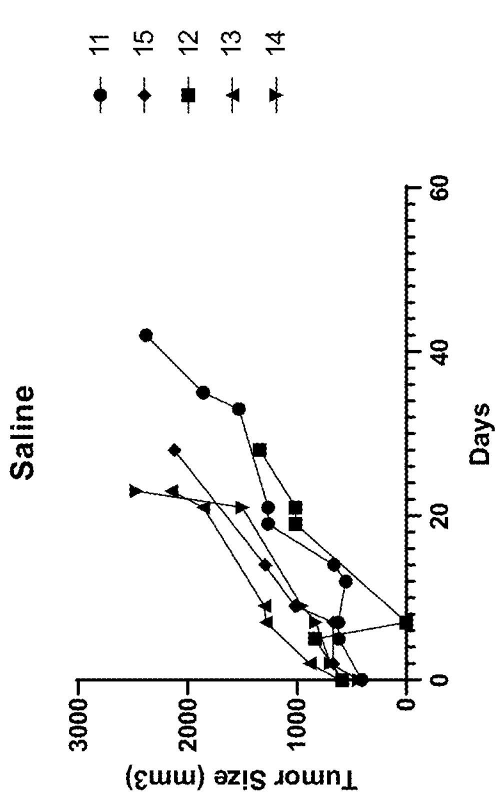
FIG. 7I shows in vivo efficacy of saline solution in mice.
Figure 7K:
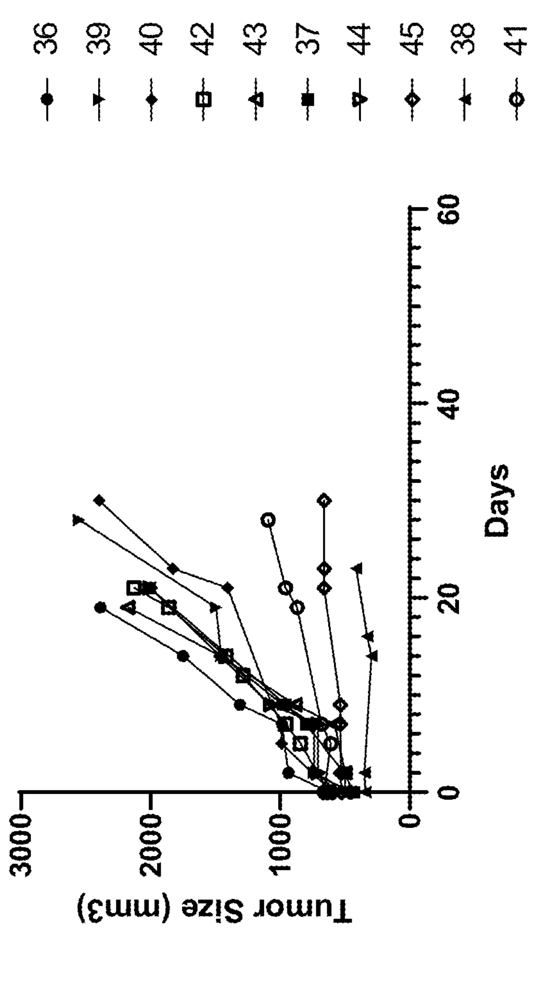
FIG. 7K shows in vivo efficacy of NTP (nab-non-toxic paclitaxel nanoparticles) in mice.

The cytotoxicity of doxorubicin and doxorubicin Nab (where non-toxic paclitaxel derivative was used to prepare the nanoparticles as described above) was tested against Daudi human B-cell lymphoma cells. $2\times10^5$ Daudi cells were plated in each well of a 24 well plate in DMEM media with 10% fetal calf serum (FCS). Daudi cells were incubated overnight at 37° C. and 5% $CO_2$ with 1, 5, 10, or 50 mg/ml of doxorubicin or doxorubicin Nab nanoparticles, and 10 mM of 5-Ethynyl-2'-deoxyuridine (EdU) was also included in each well. After the overnight incubation, the cells were harvested and fixed in 4% paraformaldehyde. After fixation, the cells are permeabilized with detergent (10% saponin) and stained with Alexa Fluor 647 conjugated anti-EdU antibody as per manufacturer's instructions (Invitrogen, Cat #C10634). Enumeration of Alexa Fluor 647 positive, proliferating cells was done by flow cytometry (Guava 8HT, Millipore). FIG. 6B shows the concentration of the drug in the nanoparticles (X-axis) vs. proliferation index of Daudi cells (Y-axis). The proliferation index was calculated by dividing the percent positive in the test wells by percent positive in the untreated (maximum proliferation), EdU labeled cells. The doxorubicin Nab nanoparticles had comparable cytotoxicity to doxorubicin at lower concentrations, but at 50 mg/ml doxorubicin Nab is more cytotoxic. Importantly, there was no loss of toxicity of doxorubicin, at any concentration, as a result of inclusion of the drug in the nanoparticles.

Example 6 In Vivo Efficacy of PDL1-SN38 Nab (Made with Non-Toxic Paclitaxel)

Female athymic nude mice, 6 weeks of age, were purchased from Envigo Corporation.

Human breast cancer cell lines MDA-MB-231 were purchased from ATCC and were cultured and expanded in DMEM medium supplemented with 10% FBS, 100 units/ml of penicillin and 100 μg/ml of streptomycin at 37° C. in a 5% $CO_2$ humidified environment for a period of 2-3 weeks before harvesting for implantation. Cell viability determined by Trypan blue dye exclusion assay was >90% before implantation. 4 million MDA-MB-231 cells in 100 μl of PBS were inoculated to the right upper flank of each mouse by s.c. injection.

Tumor volume measurement was started at day 25 after tumor cell inoculation and performed twice weekly. The longest longitudinal diameter as length and the widest transverse diameter as width were measured by using a digital caliper. Tumor volume (TV) was then calculated by the formula: $TV=[\text{length}\times(\text{width})^2]/2$ and were analyzed in Excel.

The treatment was started when average tumor size reached ~400 $mm^3$.

Mice were euthanized when tumor size reached 2000 $mm^3$.

After tumor-bearing mice were randomized, 0.9% saline, anti-PDL1, Irinotecan 15, albumin bound non-toxic paclitaxel (NTP), free SN-38 at 7.5 and 15 mg/kg (SN38 7.5 and 15), albumin bound SN-38 at 7.5 and 15 mg/kg (Nab 7.5 and 15), anti-PDL1 plus SN38 Nab delivered at the same time in separate injections (PDL1+Nab15), or anti-PDL1 coated albumin bound SN-38 at 7.5 and 15 mg/kg (NIC 7.5 and NIC 15) were administered. Albumin bound SN-38 (Nab) and anti-PDL1 coated SN-38 Nab (NIC) were made as described above. Drugs were diluted in 0.9% saline and administered to the athymic nude mice in 100 μl by IV injections in the tail vein. SN-38 in all forms was given at 7.5 and 15 mg/kg in a single dose.

Figure 8:
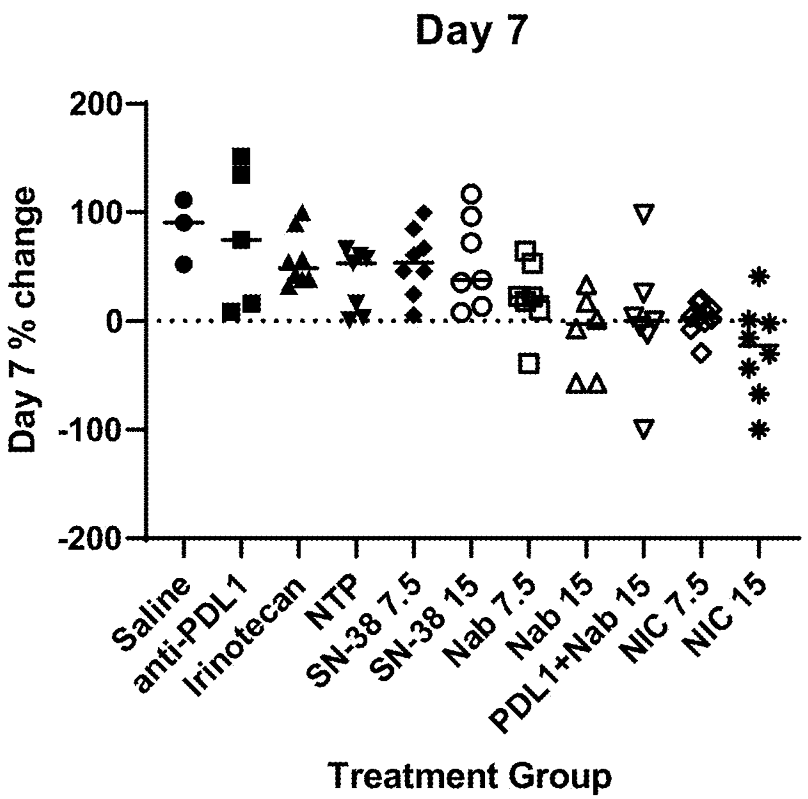
FIG. 8 shows day 7 tumor response in mice injected with MDA-MB-231 cells and treated with: saline, anti-PDL1, irinotecan, NTP, SN38 7.5, SN38 15, Nab 7.5, Nab 15, PDL1+Nab 15, NIC 7.5, or NIC 15.

Raw data of tumor measurements (FIG. 7A-FIG. 7K) were analyzed in Excel. Tumor growth curves, day 7 tumor response and Kaplan-Meier survival curves were plotted using GraphPad Prism 8.0 software. Data from day 7 tumor response were compared using student's t-test. P values of less than 0.05 were considered significant (FIG. 8).

In MDA-MB-231 tumor xenograft model tumor responses were determined at day 7 using the equation: {(tumor size day 0-tumor size day 7)/tumor size day 0}*100. Differences in tumor response were determined by student's t-test in GraphPad Prism software 8.0. Percent change above the zero line indicates tumor growth, and below the zero line indicates tumor shrinking. The NIC 15 group showed significantly higher tumor response when compared to all other groups (p-values 0.03 or less) except Nab 15 (p-value=0.49) and NIC 7.5 (p-value=0.06). This data suggests that SN-38 at 15 mg/ml are equally effective whether targeted with anti-PDL1 or not; however, increasing drug dosage from 7.5 mg/kg to 15 mg/kg in the context of the NIC is treading towards significance. Comparisons were also made between free SN38 at both doses to Nab and NIC at the same doses. The difference between NIC 7.5 and free SN38 7.5 is highly significant (p-value=0.0002) while the difference between the Nab 7.5 and the free SN38 7.5 did not reach significance (p-value=0.07). When comparing free SN38 at 15 mg/kg and the Nab 15 and NIC 15 are both significant with p-values of 0.013 and 0.0028, respectively.

Figure 9:
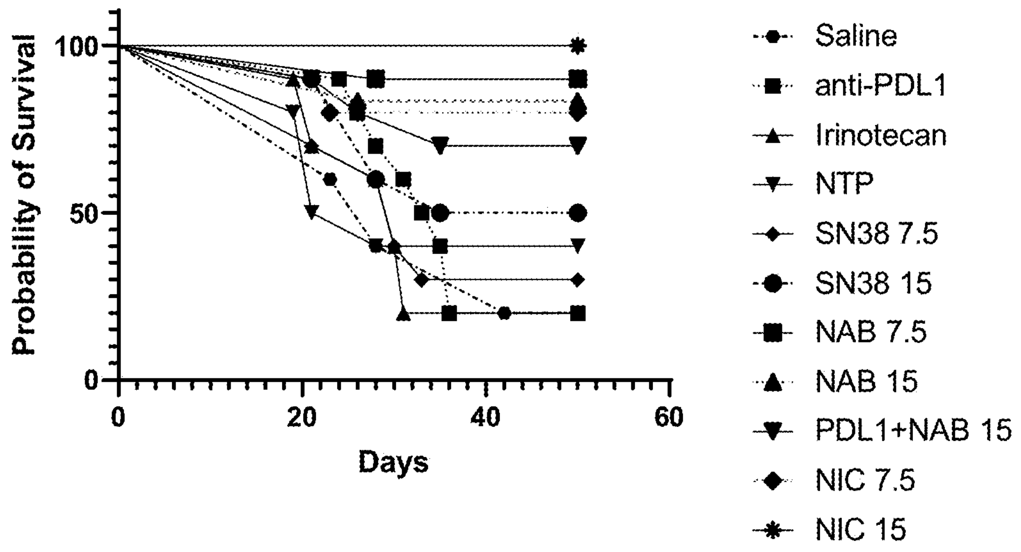
FIG. 9 shows Kaplan Meier survival curves of mice injected with MDA-MB-231 cells and treated with: saline, anti-PDL1, irinotecan, NTP, SN38 7.5, SN38 15, Nab 7.5, Nab 15, PDL1+Nab 15, NIC 7.5, or NIC 15.

Kaplan Meier curves for the MDA-MB-231 xenotransplant model were generated in GraphPad Prism software 8.0 and median survival was determined to be 28, 34, 30, 24.5, 30, and 42.5 for the saline, anti-PDL1, Irinotecan 15, NTP, free SN38 7.5, and free SN38 15, respectively. Median survival in all groups containing SN38 in the Nab or NIC remained undetermined (median survival not yet reached). The difference in survival between these groups was found to be significantly different by the Mantel-Cox log rank test with a p-value of 0.0003 (FIG. 9). Only treatment with NIC 15 resulted in 100% survival.

The foregoing examples are illustrative of the present invention, and are not to be construed as limiting thereof. Although the invention has been described in detail with reference to preferred embodiments, variations and modifications exist within the scope and spirit described herein as described and defined in the following claims.

What is claimed is:

1. A nanoparticle complex comprising albumin, bevacizumab, a therapeutically effective amount of oxaliplatin, a therapeutically effective amount of ramucirumab or ranibizumab, and paclitaxel, wherein the nanoparticle complex has anti-cancer binding specificity.

2. A nanoparticle complex comprising albumin, bevacizumab, a therapeutically effective amount of oxaliplatin, a therapeutically effective amount of ramucirumab or ranibizumab, and 20-acetoxy-4-deacetyl-5-epi-20, O-secotaxol, wherein the nanoparticle complex has anti-cancer binding specificity.

3. The nanoparticle complex of claim 1, said complex having a diameter of between 0.05 μm and 1.0 μm.

4. The nanoparticle complex of claim 3, said complex having a diameter of between 0.05 μm and 0.6 μm.

5. A pharmaceutical composition comprising a pharmaceutically acceptable carrier and the nanoparticle complexes of claim 1.

6. A pharmaceutical composition comprising a pharmaceutically acceptable carrier and the nanoparticle complexes of claim 2.

7. A lyophilized composition comprising the nanoparticle complexes of claim 1, said nanoparticle complexes being lyophilized, and wherein upon reconstitution with an aqueous solution the nanoparticle complexes are capable of binding to the anti-cancer epitope in vivo.

8. A lyophilized composition comprising the nanoparticle complexes of claim 2, said nanoparticle complexes being lyophilized, and wherein upon reconstitution with an aqueous solution the nanoparticle complexes are capable of binding to the anti-cancer epitope in vivo.

* * * * *